US012758707B2

(12) United States Patent
Diianni et al.

(10) Patent No.: US 12,758,707 B2
(45) **Date of Patent: *Oct. 13, 2026**

(54) FLUID DELIVERY DEVICE, TRANSCUTANEOUS ACCESS TOOL AND FLUID DRIVE MECHANISM FOR USE THEREWITH

(71) Applicant: Insulet Corporation, Acton, MA (US)

(72) Inventors: Steven Diianni, Danvers, MA (US); Ian Mclaughlin, Groton, MA (US); Jason O'Connor, Acton, MA (US); Robert Campbell, Waltham, MA (US); Kevin Schmid, Boxford, MA (US)

(73) Assignee: Insulet Corporation, Acton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/237,860

(22) Filed: Jun. 13, 2025

(65) Prior Publication Data

US 2025/0303058 A1 Oct. 2, 2025

Related U.S. Application Data

(63) Continuation of application No. 17/580,913, filed on Jan. 21, 2022, now Pat. No. 12,329,928, which is a (Continued)

(51) Int. Cl.

*A61M 5/145* (2006.01)
*A61B 5/145* (2006.01)

(Continued)

(52) U.S. Cl.

CPC ..... *A61M 5/14566* (2013.01); *A61B 5/14532* (2013.01); *A61B 5/14865* (2013.01);

(Continued)

(58) Field of Classification Search

CPC .. A61M 5/142; A61M 5/14216; A61M 5/145; A61M 5/1452; A61M 5/1456;

(Continued)

(56) References Cited

U.S. PATENT DOCUMENTS 303,013 A 8/1884 Horton
306,691 A 10/1884 Johnson.

(Continued)

FOREIGN PATENT DOCUMENTS

AU 2015200834 A1 3/2015
AU 2015301146 A1 3/2017

(Continued)

OTHER PUBLICATIONS

US 5,954,699 A, 09/1999, Jost et al. (withdrawn)

(Continued)

*Primary Examiner* — Kenneth J Hansen
(74) *Attorney, Agent, or Firm* — TraskBritt

(57) ABSTRACT

A fluid delivery device comprising a fluid reservoir; a transcutaneous access tool fluidly coupled to the fluid reservoir; and a drive mechanism for driving fluid from the reservoir, the drive mechanism comprising a plunger received in the reservoir; a leadscrew extending from the plunger; a nut threadably engaged with the leadscrew; a drive wheel; and a clutch mechanism coupled to the drive wheel, wherein the clutch mechanism is configured to allow the nut to pass through when disengaged and is configured to grip the nut when engaged such that the drive wheel rotates the nut to advance the drive rod and the plunger into the reservoir.

21 Claims, 6 Drawing Sheets

Related U.S. Application Data continuation of application No. 16/552,492, filed on Aug. 27, 2019, now Pat. No. 11,229,741, which is a continuation of application No. 15/226,510, filed on Aug. 2, 2016, now Pat. No. 10,420,883, which is a continuation of application No. 13/854,456, filed on Apr. 1, 2013, now Pat. No. 9,402,950, which is a continuation of application No. PCT/US2013/034674, filed on Mar. 29, 2013.

(60) Provisional application No. 61/618,028, filed on Mar. 30, 2012.

(51) Int. Cl.
*A61B 5/1486* (2006.01)
*A61M 5/14* (2006.01)
*A61M 5/142* (2006.01)
*A61M 5/158* (2006.01)
*A61M 5/172* (2006.01)
*A61M 5/32* (2006.01)
*B65D 83/761* (2025.01)
*F04B 9/02* (2006.01)

(52) U.S. Cl.
CPC .... *A61M 5/14244* (2013.01); *A61M 5/14248* (2013.01); *A61M 5/1452* (2013.01); *A61M 5/158* (2013.01); *A61M 5/1723* (2013.01); *B65D 83/761* (2025.01); *F04B 9/02* (2013.01); *A61M 2005/1403* (2013.01); *A61M 2005/14252* (2013.01); *A61M 2005/14506* (2013.01); *A61M 5/3291* (2013.01); *A61M 2230/201* (2013.01); *F04C 2270/041* (2013.01)

(58) Field of Classification Search
CPC .... A61M 5/14566; A61M 2005/14573; A61M 5/31511; A61M 5/315333; A61M 5/31535; A61M 5/315676; A61M 5/31586; F04B 9/02; B65D 83/0011; B65D 83/0027; B65D 83/0016; B05C 17/01103; B05C 17/0133; A45D 40/04
USPC .......................................... 417/319; 222/390
See application file for complete search history.

(56) References Cited

U.S. PATENT DOCUMENTS 315,727 A 4/1885 Church
405,524 A 6/1889 Benton.
410,817 A 9/1889 Weeks, Jr.
445,545 A 2/1891 Crane
588,583 A 8/1897 Lade
1,255,786 A * 2/1918 Phillips ................ B65D 83/761 222/388
1,441,508 A 1/1923 Marius et al.
2,198,666 A 4/1940 Gruskin
2,283,925 A 5/1942 Harvey
2,667,986 A 2/1954 Perelson
2,752,918 A 7/1956 Johannes
2,797,149 A 6/1957 Skeggs
2,886,529 A 5/1959 Guillaud
3,111,822 A 11/1963 Hansen
3,176,712 A 4/1965 Ramsden
3,297,260 A 1/1967 Barlow
3,413,573 A 11/1968 Nathanson et al.
3,464,359 A 9/1969 King et al.
3,505,809 A 4/1970 Sherwood
3,574,114 A 4/1971 Monforte
3,614,554 A 10/1971 Shield et al.
3,631,847 A 1/1972 Hobbs
3,634,039 A 1/1972 Brondy
3,792,703 A 2/1974 Moorehead
3,812,843 A 5/1974 Wootten et al.
3,841,328 A 10/1974 Jensen
3,858,581 A 1/1975 Kamen
3,885,662 A 5/1975 Schaefer
3,946,732 A 3/1976 Hurscham
3,947,692 A 3/1976 Payne
3,963,380 A 6/1976 Thomas et al.
3,983,077 A 9/1976 Fuller et al.
3,993,061 A 11/1976 O'Leary
3,993,226 A * 11/1976 Pavenick ............... A45D 40/04 222/327
4,055,175 A 10/1977 Clemens et al.
4,059,110 A 11/1977 Wuthrich et al.
4,067,000 A 1/1978 Carlson
4,108,177 A 8/1978 Pistor
4,146,029 A 3/1979 Ellinwood, Jr.
4,151,845 A 5/1979 Clemens
4,152,098 A 5/1979 Clark et al.
4,193,397 A 3/1980 Prosl et al.
4,210,173 A 7/1980 Choksi et al.
4,211,998 A 7/1980 Junginger et al.
4,221,219 A 9/1980 Tucker
4,231,019 A 10/1980 Junginger et al.
4,245,634 A 1/1981 Albisser et al.
4,248,377 A 2/1981 Jakobsen
4,257,324 A 3/1981 Stefansson et al.
4,261,388 A 4/1981 Shelton
4,265,601 A 5/1981 Mandroian
4,268,150 A 5/1981 Chen
4,276,170 A 6/1981 Vaillancourt
4,277,226 A 7/1981 Archibald
4,295,176 A 10/1981 Wittwer
4,313,439 A 2/1982 Babb et al.
4,342,311 A 8/1982 Whitney et al.
4,346,385 A 8/1982 Schiavone et al.
4,364,385 A 12/1982 Lossef
4,368,980 A 1/1983 Aldred et al.
4,371,790 A 2/1983 Manning et al.
4,373,527 A 2/1983 Fischell
4,400,683 A 8/1983 Eda et al.
4,403,984 A 9/1983 Ash et al.
4,417,889 A 11/1983 Choi
4,424,720 A 1/1984 Bucchianeri
4,435,173 A 3/1984 Siposs et al.
4,464,170 A 8/1984 Clemens et al.
4,469,481 A 9/1984 Kobayashi
4,475,901 A 10/1984 Kraegen et al.
4,475,905 A 10/1984 Himmelstrup
4,498,843 A 2/1985 Schneider et al.
4,507,115 A 3/1985 Kambara et al.
4,514,732 A 4/1985 Hayes, Jr.
4,523,170 A 6/1985 Huth, III
4,526,568 A 7/1985 Clemens et al.
4,526,569 A 7/1985 Bernardi
4,529,401 A 7/1985 Leslie et al.
4,551,134 A 11/1985 Slavik et al.
4,559,033 A 12/1985 Stephen et al.
4,559,037 A 12/1985 Franetzki et al.
4,560,979 A 12/1985 Rosskopf
4,562,751 A 1/1986 Nason et al.
4,567,549 A 1/1986 Lemme
4,573,968 A 3/1986 Parker
4,585,439 A 4/1986 Michel
4,601,707 A 7/1986 Albisser et al.
4,624,661 A 11/1986 Arimond
4,633,878 A 1/1987 Bombardieri
4,634,427 A 1/1987 Hannula et al.
4,646,038 A 2/1987 Wanat
4,657,529 A 4/1987 Prince et al.
4,671,429 A 6/1987 Spaanderman et al.
4,678,408 A 7/1987 Nason et al.
4,684,368 A 8/1987 Kenyon
4,685,903 A 8/1987 Cable et al.
4,731,726 A 3/1988 Allen, III
4,734,092 A 3/1988 Millerd
4,743,243 A 5/1988 Vaillancourt
4,755,169 A 7/1988 Sarnoff et al.
4,755,173 A 7/1988 Konopka et al.
4,759,120 A 7/1988 Bernstein

(56) References Cited

U.S. PATENT DOCUMENTS 4,766,889 A 8/1988 Trick et al.
4,781,688 A 11/1988 Thoma et al.
4,781,693 A 11/1988 Martinez et al.
4,801,957 A 1/1989 Vandemoere
4,808,161 A 2/1989 Kamen
4,836,752 A 6/1989 Burkett
4,846,797 A 7/1989 Howson et al.
4,854,170 A 8/1989 Brimhall et al.
4,855,746 A 8/1989 Stacy
4,858,619 A 8/1989 Toth
4,859,492 A 8/1989 Rogers et al.
4,871,351 A 10/1989 Feingold
4,880,770 A 11/1989 Mir et al.
4,882,600 A 11/1989 Van de Moere
4,886,499 A 12/1989 Cirelli et al.
4,898,578 A 2/1990 Rubalcaba, Jr.
4,898,579 A 2/1990 Groshong et al.
4,898,585 A 2/1990 Borsanyi et al.
4,900,292 A 2/1990 Berry et al.
4,908,017 A 3/1990 Howson et al.
4,919,596 A 4/1990 Slate et al.
4,925,444 A 5/1990 Orkin et al.
4,940,527 A 7/1990 Kazlauskas et al.
4,944,659 A 7/1990 Labbe et al.
4,967,201 A 10/1990 Rich, III
4,969,874 A 11/1990 Michel et al.
4,973,998 A 11/1990 Gates
4,975,581 A 12/1990 Robinson et al.
4,976,720 A 12/1990 Machold et al.
4,981,140 A 1/1991 Wyatt
4,985,016 A 1/1991 Theeuwes et al.
4,991,743 A 2/1991 Walker
4,994,047 A 2/1991 Walker et al.
5,007,286 A 4/1991 Malcolm et al.
5,007,458 A 4/1991 Marcus et al.
5,020,325 A 6/1991 Henault
5,045,871 A 9/1991 Reinholdson
5,061,424 A 10/1991 Karimi et al.
5,062,841 A 11/1991 Siegel
5,084,749 A 1/1992 Losee et al.
5,097,122 A 3/1992 Colman et al.
5,097,834 A 3/1992 Skrabal
5,101,679 A 4/1992 Smith et al.
5,102,406 A 4/1992 Arnold
5,109,850 A 5/1992 Blanco et al.
5,125,415 A 6/1992 Bell
5,130,675 A 7/1992 Sugawara
5,134,079 A 7/1992 Cusack et al.
5,139,999 A 8/1992 Gordon et al.
5,147,311 A 9/1992 Pickhard
5,153,827 A 10/1992 Coutre et al.
5,154,973 A 10/1992 Imagawa et al.
5,165,406 A 11/1992 Wong
5,176,662 A 1/1993 Bartholomew et al.
5,178,609 A 1/1993 Ishikawa
5,189,609 A 2/1993 Tivig et al.
5,198,824 A 3/1993 Poradish
5,205,819 A 4/1993 Ross et al.
5,207,642 A 5/1993 Orkin et al.
5,213,483 A 5/1993 Flaherty et al.
5,217,754 A 6/1993 Santiago-Aviles et al.
5,219,099 A 6/1993 Spence et al.
5,219,377 A 6/1993 Poradish
5,222,362 A 6/1993 Maus et al.
5,232,439 A 8/1993 Campbell et al.
5,236,416 A 8/1993 Mcdaniel et al.
5,237,993 A 8/1993 Skrabal
5,239,326 A 8/1993 Takai
5,244,463 A 9/1993 Cordner et al.
5,245,447 A 9/1993 Stemmle
5,254,096 A 10/1993 Rondelet et al.
5,257,980 A 11/1993 Van et al.
5,261,882 A 11/1993 Sealfon
5,261,884 A 11/1993 Stern et al.
5,263,198 A 11/1993 Geddes et al.
5,272,485 A 12/1993 Mason et al.
5,273,517 A 12/1993 Barone et al.
5,277,338 A 1/1994 Divall
5,281,202 A 1/1994 Weber et al.
5,281,808 A 1/1994 Kunkel
5,299,571 A 4/1994 Mastrototaro
5,308,335 A 5/1994 Ross et al.
5,308,982 A 5/1994 Ivaldi et al.
5,312,337 A 5/1994 Flaherty et al.
5,318,540 A 6/1994 Athayde et al.
5,342,298 A 8/1994 Michaels et al.
5,342,313 A 8/1994 Campbell et al.
5,346,476 A 9/1994 Elson
5,364,342 A 11/1994 Beuchat et al.
5,377,674 A 1/1995 Kuestner
5,380,665 A 1/1995 Cusack et al.
5,385,539 A 1/1995 Maynard
5,388,615 A 2/1995 Edlund et al.
5,389,078 A 2/1995 Zalesky et al.
5,403,797 A 4/1995 Ohtani et al.
5,411,480 A 5/1995 Kriesel
5,411,889 A 5/1995 Hoots et al.
5,421,812 A 6/1995 Langley et al.
5,427,988 A 6/1995 Sengupta et al.
5,433,710 A 7/1995 Vanantwerp et al.
5,452,033 A 9/1995 Balling et al.
5,456,945 A 10/1995 Mcmillan et al.
5,468,727 A 11/1995 Phillips et al.
5,478,610 A 12/1995 Desu et al.
5,492,534 A 2/1996 Athayde et al.
5,503,628 A 4/1996 Fetters et al.
5,505,709 A 4/1996 Funderburk et al.
5,505,828 A 4/1996 Wong et al.
5,507,288 A 4/1996 Boecker et al.
5,513,382 A 4/1996 Agahi-Kesheh et al.
5,514,096 A 5/1996 Hiejima
5,520,661 A 5/1996 Lal et al.
5,533,389 A 7/1996 Kamen et al.
5,535,445 A 7/1996 Gunton
5,540,772 A 7/1996 Mcmillan et al.
5,543,773 A 8/1996 Evans et al.
5,545,152 A 8/1996 Funderburk et al.
5,558,640 A 9/1996 Pfeiler et al.
5,569,186 A 10/1996 Lord et al.
5,573,342 A 11/1996 Patalano
5,575,770 A 11/1996 Melsky et al.
5,576,781 A 11/1996 Deleeuw
5,582,593 A 12/1996 Hultman
5,584,053 A 12/1996 Kommrusch et al.
5,584,813 A 12/1996 Livingston et al.
5,590,387 A 12/1996 Schmidt et al.
5,609,572 A 3/1997 Lang
5,613,956 A 3/1997 Patterson et al.
5,614,252 A 3/1997 Mcmillan et al.
5,618,269 A 4/1997 Jacobsen et al.
5,625,365 A 4/1997 Tom et al.
5,628,309 A 5/1997 Brown
5,630,710 A 5/1997 Tune et al.
5,635,433 A 6/1997 Sengupta
5,637,095 A 6/1997 Nason et al.
5,643,213 A 7/1997 Mcphee
5,647,853 A 7/1997 Feldmann et al.
5,665,065 A 9/1997 Colman et al.
5,665,070 A 9/1997 Mcphee
5,678,539 A 10/1997 Schubert et al.
5,685,844 A 11/1997 Marttila
5,685,859 A 11/1997 Kornerup
5,693,018 A 12/1997 Kriesel et al.
5,695,474 A 12/1997 Daugherty
5,695,490 A 12/1997 Flaherty et al.
5,697,899 A 12/1997 Hillman et al.
5,700,695 A 12/1997 Yassinzadeh et al.
5,702,363 A 12/1997 Flaherty
5,703,364 A 12/1997 Rosenthal
5,704,520 A 1/1998 Gross
5,707,459 A 1/1998 Itoyama et al.
5,707,715 A 1/1998 Derochemont et al.
5,713,875 A 2/1998 Tanner, II
5,714,123 A 2/1998 Sohrab

(56) References Cited

U.S. PATENT DOCUMENTS

| | | | |
|---|---|---|---|
| 5,716,343 | A | 2/1998 | Kriesel et al. |
| 5,722,397 | A | 3/1998 | Eppstein |
| 5,726,404 | A | 3/1998 | Brody |
| 5,726,751 | A | 3/1998 | Altendorf et al. |
| 5,741,228 | A | 4/1998 | Lambrecht et al. |
| 5,746,217 | A | 5/1998 | Erickson et al. |
| 5,747,350 | A | 5/1998 | Sattler |
| 5,747,870 | A | 5/1998 | Pedder |
| 5,748,827 | A | 5/1998 | Holl et al. |
| 5,755,682 | A | 5/1998 | Knudson et al. |
| 5,758,643 | A | 6/1998 | Wong et al. |
| 5,759,923 | A | 6/1998 | Mcmillan et al. |
| 5,764,159 | A | 6/1998 | Neftel |
| 5,764,189 | A | 6/1998 | Lohninger |
| 5,771,567 | A | 6/1998 | Pierce et al. |
| 5,776,103 | A | 7/1998 | Kriesel et al. |
| 5,779,676 | A | 7/1998 | Kriesel et al. |
| 5,785,681 | A | 7/1998 | Indravudh |
| 5,785,688 | A | 7/1998 | Joshi et al. |
| 5,797,881 | A | 8/1998 | Gadot |
| 5,800,397 | A | 9/1998 | Wilson et al. |
| 5,800,405 | A | 9/1998 | Mcphee |
| 5,800,420 | A | 9/1998 | Gross et al. |
| 5,801,057 | A | 9/1998 | Smart et al. |
| 5,804,048 | A | 9/1998 | Wong et al. |
| 5,807,075 | A | 9/1998 | Jacobsen et al. |
| 5,810,015 | A | 9/1998 | Flaherty |
| 5,814,020 | A | 9/1998 | Gross |
| 5,817,007 | A | 10/1998 | Fodgaard et al. |
| 5,820,622 | A | 10/1998 | Gross et al. |
| 5,823,951 | A | 10/1998 | Messerschmidt |
| 5,839,467 | A | 11/1998 | Saaski et al. |
| 5,840,020 | A | 11/1998 | Heinonen et al. |
| 5,840,063 | A | 11/1998 | Flaherty |
| D403,313 | S | 12/1998 | Peppel |
| 5,845,218 | A | 12/1998 | Altschul |
| 5,848,990 | A | 12/1998 | Cirelli et al. |
| 5,848,991 | A | 12/1998 | Gross et al. |
| 5,851,197 | A | 12/1998 | Marano et al. |
| 5,854,608 | A | 12/1998 | Leisten |
| 5,858,005 | A | 1/1999 | Kriesel |
| 5,858,239 | A | 1/1999 | Kenley et al. |
| 5,859,621 | A | 1/1999 | Leisten |
| 5,865,806 | A | 2/1999 | Howell |
| 5,871,470 | A | 2/1999 | Mcwha |
| 5,875,393 | A | 2/1999 | Altschul et al. |
| 5,878,539 | A | 3/1999 | Grubb |
| 5,879,310 | A | 3/1999 | Sopp et al. |
| 5,885,659 | A | 3/1999 | Takahashi et al. |
| 5,885,808 | A | 3/1999 | Spooner et al. |
| 5,886,647 | A | 3/1999 | Badger et al. |
| 5,889,459 | A | 3/1999 | Hattori et al. |
| 5,891,097 | A | 4/1999 | Saito et al. |
| 5,892,489 | A | 4/1999 | Kanba et al. |
| 5,897,530 | A | 4/1999 | Jackson |
| 5,902,253 | A | 5/1999 | Pfeiffer et al. |
| 5,903,421 | A | 5/1999 | Furutani et al. |
| 5,906,597 | A | 5/1999 | Mcphee |
| 5,911,716 | A | 6/1999 | Rake et al. |
| 5,919,167 | A | 7/1999 | Mulhauser et al. |
| 5,921,419 | A | 7/1999 | Niedospial et al. |
| 5,931,814 | A | 8/1999 | Alex et al. |
| 5,932,175 | A | 8/1999 | Knute et al. |
| 5,933,121 | A | 8/1999 | Rainhart et al. |
| 5,935,099 | A | 8/1999 | Peterson et al. |
| 5,945,963 | A | 8/1999 | Leisten |
| 5,947,911 | A | 9/1999 | Wong et al. |
| 5,954,058 | A | 9/1999 | Flaherty |
| 5,954,694 | A | 9/1999 | Sunseri |
| 5,957,859 | A | 9/1999 | Rosenfeld |
| 5,957,890 | A | 9/1999 | Mann et al. |
| 5,961,492 | A | 10/1999 | Kriesel et al. |
| 5,965,848 | A | 10/1999 | Altschul et al. |
| 5,971,941 | A | 10/1999 | Simons et al. |
| 5,971,963 | A | 10/1999 | Choi |
| 5,983,094 | A | 11/1999 | Altschul et al. |
| 5,993,423 | A | 11/1999 | Choi |
| 5,997,501 | A | 12/1999 | Gross et al. |
| 6,005,151 | A | 12/1999 | Herrmann et al. |
| 6,017,318 | A | 1/2000 | Gauthier et al. |
| 6,019,747 | A | 2/2000 | Mcphee |
| 6,023,251 | A | 2/2000 | Koo et al. |
| 6,024,539 | A | 2/2000 | Blomquist |
| 6,027,826 | A | 2/2000 | Derochemont et al. |
| 6,028,568 | A | 2/2000 | Asakura et al. |
| 6,031,445 | A | 2/2000 | Marty et al. |
| 6,032,059 | A | 2/2000 | Henning et al. |
| 6,036,924 | A | 3/2000 | Simons et al. |
| 6,040,578 | A | 3/2000 | Malin et al. |
| 6,040,805 | A | 3/2000 | Huynh et al. |
| 6,046,707 | A | 4/2000 | Gaughan et al. |
| 6,049,727 | A | 4/2000 | Crothall |
| 6,050,457 | A | 4/2000 | Arnold et al. |
| 6,050,978 | A | 4/2000 | Orr et al. |
| 6,052,040 | A | 4/2000 | Hino |
| 6,058,934 | A | 5/2000 | Sullivan |
| 6,066,103 | A | 5/2000 | Duchon et al. |
| 6,068,615 | A | 5/2000 | Brown et al. |
| 6,071,292 | A | 6/2000 | Makower et al. |
| 6,072,180 | A | 6/2000 | Kramer et al. |
| 6,074,369 | A | 6/2000 | Sage et al. |
| 6,077,055 | A | 6/2000 | Vilks |
| 6,086,615 | A | 7/2000 | Wood et al. |
| 6,090,092 | A | 7/2000 | Fowles et al. |
| 6,101,406 | A | 8/2000 | Hacker et al. |
| 6,102,872 | A | 8/2000 | Doneen et al. |
| 6,111,544 | A | 8/2000 | Dakeya et al. |
| 6,115,673 | A | 9/2000 | Malin et al. |
| 6,123,827 | A | 9/2000 | Wong et al. |
| 6,124,134 | A | 9/2000 | Stark |
| 6,126,637 | A | 10/2000 | Kriesel et al. |
| 6,128,519 | A | 10/2000 | Say |
| 6,142,939 | A | 11/2000 | Eppstein et al. |
| 6,143,164 | A | 11/2000 | Heller et al. |
| 6,143,432 | A | 11/2000 | De et al. |
| 6,144,847 | A | 11/2000 | Altschul et al. |
| 6,152,898 | A | 11/2000 | Olsen |
| 6,154,176 | A | 11/2000 | Fathy et al. |
| 6,157,041 | A | 12/2000 | Thomas et al. |
| 6,159,188 | A | 12/2000 | Laibovitz et al. |
| 6,161,028 | A | 12/2000 | Braig et al. |
| 6,162,639 | A | 12/2000 | Douglas |
| 6,174,300 | B1 | 1/2001 | Kriesel et al. |
| 6,176,004 | B1 | 1/2001 | Rainhart et al. |
| 6,181,297 | B1 | 1/2001 | Leisten |
| 6,188,368 | B1 | 2/2001 | Koriyama et al. |
| 6,190,359 | B1 | 2/2001 | Heruth |
| 6,195,049 | B1 | 2/2001 | Kim et al. |
| 6,196,046 | B1 | 3/2001 | Braig et al. |
| 6,200,287 | B1 | 3/2001 | Keller et al. |
| 6,200,293 | B1 | 3/2001 | Kriesel et al. |
| 6,200,338 | B1 | 3/2001 | Solomon et al. |
| 6,204,203 | B1 | 3/2001 | Narwankar et al. |
| 6,206,850 | B1 | 3/2001 | O'Neil |
| 6,208,843 | B1 | 3/2001 | Huang et al. |
| 6,214,629 | B1 | 4/2001 | Freitag et al. |
| 6,222,489 | B1 | 4/2001 | Tsuru et al. |
| 6,226,082 | B1 | 5/2001 | Roe |
| 6,244,776 | B1 | 6/2001 | Wiley |
| 6,244,778 | B1 | 6/2001 | Chesbrough |
| 6,261,065 | B1 | 7/2001 | Nayak et al. |
| 6,262,798 | B1 | 7/2001 | Shepherd et al. |
| 6,266,020 | B1 | 7/2001 | Chang |
| 6,270,455 | B1 | 8/2001 | Brown |
| 6,271,045 | B1 | 8/2001 | Douglas et al. |
| 6,280,381 | B1 | 8/2001 | Malin et al. |
| 6,285,448 | B1 | 9/2001 | Kuenstner |
| 6,300,894 | B1 | 10/2001 | Lynch et al. |
| 6,309,370 | B1 | 10/2001 | Haim et al. |
| 6,312,888 | B1 | 11/2001 | Wong et al. |
| 6,320,547 | B1 | 11/2001 | Fathy et al. |
| 6,323,549 | B1 | 11/2001 | Derochemont et al. |
| 6,334,851 | B1 | 1/2002 | Hayes et al. |
| 6,352,522 | B1 | 3/2002 | Kim et al. |

(56) References Cited

U.S. PATENT DOCUMENTS 6,363,609 B1 4/2002 Pickren
6,375,627 B1 4/2002 Mauze et al.
6,375,638 B2 4/2002 Nason et al.
6,375,639 B1 4/2002 Duplessie et al.
6,379,301 B1 4/2002 Worthington et al.
6,402,689 B1 6/2002 Scarantino et al.
6,413,244 B1 7/2002 Bestetti et al.
6,470,279 B1 10/2002 Samsoondar
6,474,219 B2 11/2002 Klitmose et al.
6,475,196 B1 11/2002 Vachon
6,477,065 B2 11/2002 Parks
6,477,901 B1 11/2002 Tadigadapa et al.
6,484,044 B1 11/2002 Lilienfeld-Toal
6,485,461 B1 11/2002 Mason et al.
6,485,462 B1 11/2002 Kriesel
6,488,652 B1 12/2002 Weijand et al.
6,491,656 B1 12/2002 Morris
6,492,949 B1 12/2002 Breglia et al.
6,496,149 B1 12/2002 Birnbaum et al.
6,501,415 B1 12/2002 Viana et al.
6,512,937 B2 1/2003 Blank et al.
6,520,936 B1 2/2003 Mann
6,525,509 B1 2/2003 Petersson et al.
6,527,744 B1 3/2003 Kriesel et al.
6,528,809 B1 3/2003 Thomas et al.
6,537,249 B2 3/2003 Kriesell et al.
6,539,286 B1 3/2003 Jiang
6,540,260 B1 4/2003 Tan
6,540,672 B1 4/2003 Simonsen et al.
6,541,820 B1 4/2003 Bol
6,544,212 B2 4/2003 Galley et al.
6,546,268 B1 4/2003 Ishikawa et al.
6,546,269 B1 4/2003 Kurnik
6,552,693 B1 4/2003 Leisten
6,553,841 B1 4/2003 Blouch
6,554,798 B1 4/2003 Mann et al.
6,556,850 B1 4/2003 Braig et al.
D474,778 S 5/2003 Barnes
6,558,351 B1 5/2003 Steil et al.
6,559,735 B1 5/2003 Hoang et al.
6,560,471 B1 5/2003 Heller et al.
6,561,978 B1 5/2003 Conn et al.
6,562,001 B2 5/2003 Lebel et al.
6,562,014 B2 5/2003 Lin et al.
6,569,115 B1 5/2003 Barker et al.
6,569,125 B2 5/2003 Jepson et al.
6,572,542 B1 6/2003 Houben et al.
6,572,545 B2 6/2003 Knobbe et al.
6,572,585 B2 6/2003 Choi
6,574,490 B2 6/2003 Abbink et al.
6,575,905 B2 6/2003 Knobbe et al.
6,580,934 B1 6/2003 Braig et al.
6,583,699 B2 6/2003 Yokoyama
6,595,956 B1 7/2003 Gross et al.
6,611,419 B1 8/2003 Chakravorty
6,618,603 B2 9/2003 Varalli et al.
6,620,750 B2 9/2003 Kim et al.
6,633,772 B2 10/2003 Ford et al.
6,635,958 B2 10/2003 Bates et al.
6,639,556 B2 10/2003 Baba
6,642,908 B2 11/2003 Pleva et al.
6,645,142 B2 11/2003 Braig et al.
6,650,303 B2 11/2003 Kim et al.
6,653,091 B1 11/2003 Dunn et al.
6,656,158 B2 12/2003 Mahoney et al.
6,656,159 B2 12/2003 Flaherty
6,662,030 B2 12/2003 Khalil et al.
6,666,852 B2 12/2003 Niedospial, Jr.
6,669,663 B1 12/2003 Thompson
6,670,497 B2 12/2003 Tashino et al.
6,678,542 B2 1/2004 Braig et al.
6,680,700 B2 1/2004 Hilgers
6,683,576 B2 1/2004 Achim
6,686,406 B2 2/2004 Tomomatsu et al.
6,690,336 B1 2/2004 Leisten et al.
6,697,605 B1 2/2004 Atokawa et al.
6,699,218 B2 3/2004 Flaherty et al.
6,699,221 B2 3/2004 Vaillancourt
6,718,189 B2 4/2004 Rohrscheib et al.
6,720,926 B2 4/2004 Killen et al.
6,721,582 B2 4/2004 Trepagnier et al.
6,723,072 B2 4/2004 Flaherty et al.
6,727,785 B2 4/2004 Killen et al.
6,728,560 B2 4/2004 Kollias et al.
6,731,244 B2 5/2004 Killen et al.
6,731,248 B2 5/2004 Killen et al.
6,733,890 B2 5/2004 Imanaka et al.
6,740,059 B2 5/2004 Flaherty
6,740,072 B2 5/2004 Starkweather et al.
6,741,148 B2 5/2004 Killen et al.
6,742,249 B2 6/2004 Derochemont et al.
6,743,744 B1 6/2004 Kim et al.
6,749,407 B2 6/2004 Xie et al.
6,750,740 B2 6/2004 Killen et al.
6,750,820 B2 6/2004 Killen et al.
6,751,490 B2 6/2004 Esenaliev et al.
6,753,745 B2 6/2004 Killen et al.
6,753,814 B2 6/2004 Killen et al.
6,758,835 B2 7/2004 Close et al.
6,762,237 B2 7/2004 Glatkowski et al.
6,780,156 B2 8/2004 Haueter et al.
6,787,181 B2 9/2004 Uchiyama et al.
6,791,496 B1 9/2004 Killen et al.
6,810,290 B2 10/2004 Lebel et al.
6,826,031 B2 11/2004 Nagai et al.
6,830,623 B2 12/2004 Hayashi et al.
6,837,858 B2 1/2005 Cunningham et al.
6,837,988 B2 1/2005 Leong et al.
6,846,288 B2 1/2005 Nagar et al.
6,851,260 B2 2/2005 Morten
6,853,288 B2 2/2005 Ahn et al.
6,858,892 B2 2/2005 Yamagata
6,862,534 B2 3/2005 Sterling et al.
6,864,848 B2 3/2005 Sievenpiper
6,865,408 B1 3/2005 Abbink et al.
6,871,396 B2 3/2005 Sugaya et al.
6,878,871 B2 4/2005 Scher et al.
6,883,778 B1 4/2005 Newton et al.
6,890,291 B2 5/2005 Robinson et al.
6,905,989 B2 6/2005 Ellis et al.
6,906,674 B2 6/2005 Mckinzie et al.
6,914,566 B2 7/2005 Beard
6,919,119 B2 7/2005 Kalkan et al.
6,928,298 B2 8/2005 Furutani et al.
6,936,029 B2 8/2005 Mann et al.
6,943,430 B2 9/2005 Kwon
6,943,731 B2 9/2005 Killen et al.
6,949,081 B1 9/2005 Chance
6,958,809 B2 10/2005 Sterling et al.
6,963,259 B2 11/2005 Killen et al.
6,989,891 B2 1/2006 Braig et al.
6,990,366 B2 1/2006 Say et al.
7,002,436 B2 2/2006 Ma et al.
7,008,404 B2 3/2006 Nakajima
7,009,180 B2 3/2006 Sterling et al.
7,016,713 B2 3/2006 Gardner et al.
7,018,360 B2 3/2006 Flaherty et al.
7,025,743 B2 4/2006 Mann et al.
7,025,744 B2 4/2006 Utterberg et al.
7,027,848 B2 4/2006 Robinson et al.
7,043,288 B2 5/2006 Davis et al.
7,047,637 B2 5/2006 Derochemont et al.
7,060,059 B2 6/2006 Keith et al.
7,060,350 B2 6/2006 Takaya et al.
7,061,593 B2 6/2006 Braig et al.
7,096,124 B2 8/2006 Sterling et al.
7,104,275 B2 9/2006 Dille
7,115,205 B2 10/2006 Robinson et al.
7,116,949 B2 10/2006 Irie et al.
7,128,727 B2 10/2006 Flaherty et al.
7,137,694 B2 11/2006 Ferran et al.
7,137,964 B2 11/2006 Flaherty
7,139,593 B2 11/2006 Kavak et al.
7,139,598 B2 11/2006 Hull et al.

(56) References Cited

U.S. PATENT DOCUMENTS 7,144,384 B2 12/2006 Gorman et al.
7,160,272 B1 1/2007 Eyal et al.
7,171,252 B1 1/2007 Scarantino et al.
7,190,988 B2 3/2007 Say et al.
7,204,823 B2 4/2007 Estes et al.
7,230,316 B2 6/2007 Yamazaki et al.
7,248,912 B2 7/2007 Gough et al.
7,267,665 B2 9/2007 Steil et al.
7,271,912 B2 9/2007 Sterling et al.
7,278,983 B2 10/2007 Ireland et al.
7,291,107 B2 11/2007 Hellwig et al.
7,291,133 B1 11/2007 Kindler et al.
7,291,497 B2 11/2007 Holmes et al.
7,291,782 B2 11/2007 Sager et al.
7,303,549 B2 12/2007 Flaherty et al.
7,303,622 B2 12/2007 Loch et al.
7,303,922 B2 12/2007 Jeng et al.
7,354,420 B2 4/2008 Steil et al.
7,388,202 B2 6/2008 Sterling et al.
7,402,153 B2 7/2008 Steil et al.
7,404,796 B2 7/2008 Ginsberg
7,405,698 B2 7/2008 de Rochemont
7,429,255 B2 9/2008 Thompson
7,460,130 B2 12/2008 Salganicoff
7,481,787 B2 1/2009 Gable et al.
7,491,187 B2 2/2009 Van et al.
7,500,949 B2 3/2009 Gottlieb et al.
7,509,156 B2 3/2009 Flanders
D590,415 S 4/2009 Ball et al.
7,522,124 B2 4/2009 Smith et al.
7,547,281 B2 6/2009 Hayes et al.
7,553,512 B2 6/2009 Kodas et al.
7,564,887 B2 7/2009 Wang et al.
7,569,030 B2 8/2009 Lebel et al.
7,595,623 B2 9/2009 Bennett
7,608,042 B2 10/2009 Goldberger et al.
7,651,845 B2 1/2010 Doyle et al.
7,652,901 B2 1/2010 Kirchmeier et al.
7,680,529 B2 3/2010 Kroll
D614,634 S 4/2010 Nilsen
7,714,794 B2 5/2010 Tavassoli Hozouri
7,734,323 B2 6/2010 Blomquist et al.
7,763,917 B2 7/2010 de Rochemont
7,766,829 B2 8/2010 Sloan et al.
7,771,391 B2 8/2010 Carter
7,771,392 B2 8/2010 De et al.
7,785,258 B2 8/2010 Braig et al.
7,785,296 B2 8/2010 Muskatello et al.
7,806,854 B2 10/2010 Damiano et al.
7,806,886 B2 10/2010 Kanderian et al.
7,812,774 B2 10/2010 Friman et al.
7,914,499 B2 3/2011 Gonnelli et al.
7,918,825 B2 4/2011 O'Connor et al.
7,946,985 B2 5/2011 Mastrototaro et al.
7,951,114 B2 5/2011 Rush et al.
D640,269 S 6/2011 Chen
7,972,296 B2 7/2011 Braig et al.
8,066,805 B2 11/2011 Zuercher et al.
8,069,690 B2 12/2011 Desantolo et al.
8,114,489 B2 2/2012 Nemat-Nasser et al.
8,178,457 B2 5/2012 De Rochemont
8,193,873 B2 6/2012 Kato et al.
8,221,345 B2 7/2012 Blomquist
8,251,907 B2 8/2012 Sterling et al.
8,251,921 B2 8/2012 Briggs et al.
8,267,921 B2 9/2012 Yodfat et al.
8,350,657 B2 1/2013 Derochemont
8,354,294 B2 1/2013 De et al.
8,382,703 B1 2/2013 Abdelaal
D677,685 S 3/2013 Simmons et al.
8,449,524 B2 5/2013 Braig et al.
8,452,359 B2 5/2013 Rebec et al.
8,454,576 B2 6/2013 Mastrototaro et al.
8,467,980 B2 6/2013 Campbell et al.
8,478,557 B2 7/2013 Hayter et al.
D688,686 S 8/2013 Rhee et al.
8,499,913 B2 8/2013 Gunter
8,547,239 B2 10/2013 Peatfield et al.
D693,837 S 11/2013 Bouchier
8,593,819 B2 11/2013 De Rochemont
D695,757 S 12/2013 Ray et al.
8,597,274 B2 12/2013 Sloan et al.
8,622,988 B2 1/2014 Hayter
8,715,839 B2 5/2014 De Rochemont
D710,879 S 8/2014 Elston et al.
8,810,394 B2 8/2014 Kalpin
D714,822 S 10/2014 Capua et al.
D715,315 S 10/2014 Wood
D715,815 S 10/2014 Bortman et al.
D718,779 S 12/2014 Hang et al.
D720,366 S 12/2014 Hiltunen et al.
8,905,995 B2 12/2014 Mernoe
8,920,376 B2 12/2014 Caffey et al.
D720,765 S 1/2015 Xie et al.
8,939,935 B2 1/2015 O'Connor et al.
D726,760 S 4/2015 Yokota et al.
D727,928 S 4/2015 Allison et al.
D730,378 S 5/2015 Xiong et al.
D733,175 S 6/2015 Bae
9,061,097 B2 6/2015 Holt et al.
D734,356 S 7/2015 Xiong et al.
D736,811 S 8/2015 Teichner et al.
D737,305 S 8/2015 Scazafavo et al.
D737,831 S 9/2015 Lee
D737,832 S 9/2015 Lim et al.
D738,901 S 9/2015 Amin
D740,301 S 10/2015 Soegiono et al.
D740,308 S 10/2015 Kim et al.
D740,311 S 10/2015 Drozd et al.
D741,354 S 10/2015 Lee et al.
D741,359 S 10/2015 Ji-Hye et al.
9,171,343 B1 10/2015 Fischell et al.
D743,431 S 11/2015 Pal et al.
D743,991 S 11/2015 Pal et al.
9,180,224 B2 11/2015 Moseley et al.
9,180,244 B2 11/2015 Anderson et al.
9,192,716 B2 11/2015 Jugl et al.
D744,514 S 12/2015 Shin et al.
D744,517 S 12/2015 Pal et al.
D745,032 S 12/2015 Pal et al.
D745,034 S 12/2015 Pal et al.
D745,035 S 12/2015 Pal et al.
D746,827 S 1/2016 Jung et al.
D746,828 S 1/2016 Arai et al.
D747,352 S 1/2016 Lee et al.
9,233,204 B2 1/2016 Booth et al.
D749,097 S 2/2016 Zou et al.
D749,118 S 2/2016 Wang
D751,100 S 3/2016 Lindn et al.
D752,604 S 3/2016 Zhang
D753,134 S 4/2016 Vazquez
D754,718 S 4/2016 Zhou
D755,193 S 5/2016 Sun et al.
D755,799 S 5/2016 Finnis et al.
D755,820 S 5/2016 Wang
D756,387 S 5/2016 Chang et al.
D757,032 S 5/2016 Sabia et al.
D757,035 S 5/2016 Raskin et al.
D758,391 S 6/2016 Suarez
D758,422 S 6/2016 Zhao
D759,032 S 6/2016 Amin et al.
D759,078 S 6/2016 Iwamoto
D759,678 S 6/2016 Jung et al.
D759,687 S 6/2016 Chang et al.
D761,812 S 7/2016 Motamedi
D763,308 S 8/2016 Wang et al.
D763,868 S 8/2016 Lee et al.
D765,110 S 8/2016 Liang
D765,124 S 8/2016 Minks-Brown et al.
9,402,950 B2 8/2016 Dilanni et al.
D765,707 S 9/2016 Gomez
D766,286 S 9/2016 Lee et al.
D767,586 S 9/2016 Kwon et al.
D768,154 S 10/2016 Kim et al.

(56) References Cited

U.S. PATENT DOCUMENTS

| | | | |
|---|---|---|---|
| D768,188 | S | 10/2016 | Li et al. |
| D768,660 | S | 10/2016 | Wielgosz |
| D768,685 | S | 10/2016 | Lee et al. |
| D769,315 | S | 10/2016 | Scotti |
| D770,507 | S | 11/2016 | Umezawa et al. |
| D770,515 | S | 11/2016 | Cho et al. |
| D771,073 | S | 11/2016 | Choi et al. |
| D771,076 | S | 11/2016 | Butcher et al. |
| D771,690 | S | 11/2016 | Yin et al. |
| D772,911 | S | 11/2016 | Lee et al. |
| 9,486,571 | B2 | 11/2016 | Rosinko |
| D773,531 | S | 12/2016 | Toth et al. |
| D775,184 | S | 12/2016 | Song et al. |
| D775,196 | S | 12/2016 | Huang et al. |
| 9,520,649 | B2 | 12/2016 | De Rochemont |
| D775,658 | S | 1/2017 | Luo et al. |
| D776,126 | S | 1/2017 | Lai et al. |
| D776,687 | S | 1/2017 | Wick et al. |
| D777,191 | S | 1/2017 | Polimeni |
| D777,758 | S | 1/2017 | Kisselev et al. |
| 9,539,596 | B2 | 1/2017 | Ikushima |
| 9,579,456 | B2 | 2/2017 | Budiman et al. |
| D781,323 | S | 3/2017 | Green et al. |
| D781,781 | S | 3/2017 | Schimmoeller, Jr. |
| D781,877 | S | 3/2017 | Ko et al. |
| D781,878 | S | 3/2017 | Butcher et al. |
| D781,879 | S | 3/2017 | Butcher et al. |
| D781,903 | S | 3/2017 | Reichle et al. |
| D781,905 | S | 3/2017 | Nakaguchi et al. |
| D782,506 | S | 3/2017 | Kim et al. |
| D783,672 | S | 4/2017 | Rajasankar et al. |
| D785,010 | S | 4/2017 | Bachman et al. |
| D785,656 | S | 5/2017 | Bramer et al. |
| D786,278 | S | 5/2017 | Motamedi |
| D786,898 | S | 5/2017 | Hall |
| D788,126 | S | 5/2017 | Evnin et al. |
| 9,656,017 | B2 | 5/2017 | Greene |
| D788,621 | S | 6/2017 | Shallice et al. |
| D788,652 | S | 6/2017 | Mutsuro et al. |
| D789,402 | S | 6/2017 | Dye et al. |
| D789,967 | S | 6/2017 | Kaplan et al. |
| D789,982 | S | 6/2017 | Christiana et al. |
| D790,560 | S | 6/2017 | Inose et al. |
| D791,781 | S | 7/2017 | Donarski et al. |
| D791,805 | S | 7/2017 | Segars |
| D791,812 | S | 7/2017 | Bistoni et al. |
| D793,412 | S | 8/2017 | Chaudhri et al. |
| D795,886 | S | 8/2017 | Ng et al. |
| D795,891 | S | 8/2017 | Kohan et al. |
| D795,900 | S | 8/2017 | Bischoff et al. |
| D795,906 | S | 8/2017 | Butrick |
| D795,927 | S | 8/2017 | Bischoff et al. |
| 9,743,224 | B2 | 8/2017 | San et al. |
| D796,530 | S | 9/2017 | Mcmillan et al. |
| D796,540 | S | 9/2017 | Mclean et al. |
| D797,116 | S | 9/2017 | Chapman et al. |
| D797,763 | S | 9/2017 | Kim et al. |
| D797,774 | S | 9/2017 | Park et al. |
| D797,797 | S | 9/2017 | Gandhi et al. |
| D798,310 | S | 9/2017 | Golden et al. |
| D798,311 | S | 9/2017 | Golden et al. |
| D799,536 | S | 10/2017 | Eder |
| D800,765 | S | 10/2017 | Stoksik |
| D800,769 | S | 10/2017 | Hennessy et al. |
| D801,383 | S | 10/2017 | Park et al. |
| D802,011 | S | 11/2017 | Friedman et al. |
| D802,088 | S | 11/2017 | Bos et al. |
| D803,232 | S | 11/2017 | Leigh et al. |
| D803,242 | S | 11/2017 | Mizono et al. |
| D804,502 | S | 12/2017 | Amini et al. |
| D805,525 | S | 12/2017 | Dascola et al. |
| D806,716 | S | 1/2018 | Pahwa et al. |
| D807,376 | S | 1/2018 | Mizono et al. |
| D807,400 | S | 1/2018 | Lagreca |
| D807,910 | S | 1/2018 | Graham et al. |
| D807,918 | S | 1/2018 | Cohen et al. |
| D807,919 | S | 1/2018 | Cohen et al. |
| D808,423 | S | 1/2018 | Jiang et al. |
| D808,974 | S | 1/2018 | Chiappone et al. |
| D808,983 | S | 1/2018 | Narinedhat et al. |
| 9,857,090 | B2 | 1/2018 | Golden et al. |
| D810,116 | S | 2/2018 | Mclean et al. |
| D810,771 | S | 2/2018 | Gandhi et al. |
| 9,907,515 | B2 | 3/2018 | Doyle et al. |
| D815,131 | S | 4/2018 | Thompson et al. |
| D816,090 | S | 4/2018 | Stonecipher et al. |
| D817,339 | S | 5/2018 | Nanjappan et al. |
| D818,491 | S | 5/2018 | Timmer et al. |
| D819,057 | S | 5/2018 | Huang |
| D819,059 | S | 5/2018 | Julia |
| 9,980,140 | B1 | 5/2018 | Spencer et al. |
| 9,984,773 | B2 | 5/2018 | Gondhalekar et al. |
| D820,311 | S | 6/2018 | Cabrera et al. |
| D820,862 | S | 6/2018 | Alfonzo et al. |
| D822,034 | S | 7/2018 | Clymer et al. |
| D822,677 | S | 7/2018 | Weaver et al. |
| D822,684 | S | 7/2018 | Clausen-Stuck et al. |
| D822,692 | S | 7/2018 | Loychik et al. |
| D823,862 | S | 7/2018 | Chung et al. |
| D824,400 | S | 7/2018 | Chang et al. |
| D824,951 | S | 8/2018 | Kolbrener et al. |
| D826,956 | S | 8/2018 | Pillalamarri et al. |
| D826,957 | S | 8/2018 | Pillalamarri et al. |
| D828,381 | S | 9/2018 | Lee et al. |
| D829,732 | S | 10/2018 | Jeffrey et al. |
| D830,374 | S | 10/2018 | Leonard et al. |
| D830,384 | S | 10/2018 | Lepine et al. |
| D830,385 | S | 10/2018 | Lepine et al. |
| D830,407 | S | 10/2018 | Kisielius et al. |
| D831,033 | S | 10/2018 | Leonard et al. |
| D833,469 | S | 11/2018 | Coleman et al. |
| D834,601 | S | 11/2018 | Felt |
| D835,132 | S | 12/2018 | Ito et al. |
| D835,145 | S | 12/2018 | Cashner et al. |
| D835,147 | S | 12/2018 | Kisielius et al. |
| D835,651 | S | 12/2018 | Bao |
| D835,666 | S | 12/2018 | Saleh et al. |
| D836,123 | S | 12/2018 | Pillalamarri et al. |
| D837,807 | S | 1/2019 | Baber et al. |
| D838,731 | S | 1/2019 | Pillalamarri et al. |
| D840,418 | S | 2/2019 | Saad et al. |
| D840,419 | S | 2/2019 | Saad et al. |
| D844,022 | S | 3/2019 | Amin |
| D845,317 | S | 4/2019 | Wellmeier et al. |
| 10,248,839 | B2 | 4/2019 | Levy et al. |
| D848,459 | S | 5/2019 | Li |
| D851,099 | S | 6/2019 | Uppala et al. |
| D851,658 | S | 6/2019 | Pillalamarri et al. |
| 10,335,464 | B1 | 7/2019 | Michelich et al. |
| 10,441,723 | B2 | 10/2019 | Nazzaro |
| D865,795 | S | 11/2019 | Koo |
| D872,746 | S | 1/2020 | Laborde |
| D874,471 | S | 2/2020 | Pillalamarri et al. |
| D875,114 | S | 2/2020 | Clediere |
| 10,583,250 | B2 | 3/2020 | Mazlish et al. |
| D880,498 | S | 4/2020 | Shahidi et al. |
| D888,070 | S | 6/2020 | Yusupov et al. |
| 10,695,485 | B2 | 6/2020 | Nazzaro |
| 10,737,024 | B2 | 8/2020 | Schmid |
| D904,426 | S | 12/2020 | Paul |
| D911,353 | S | 2/2021 | Sanchez et al. |
| D914,031 | S | 3/2021 | Ding et al. |
| D916,729 | S | 4/2021 | Gabriel et al. |
| D916,870 | S | 4/2021 | Hemsley |
| D916,878 | S | 4/2021 | Kim et al. |
| 10,987,468 | B2 | 4/2021 | Mazlish et al. |
| D918,261 | S | 5/2021 | Ramamurthy et al. |
| D920,351 | S | 5/2021 | Zhang |
| D923,033 | S | 6/2021 | Smith et al. |
| D927,533 | S | 8/2021 | Clymer |
| D938,447 | S | 12/2021 | Holland |
| 11,197,964 | B2 | 12/2021 | Sjolund et al. |
| 11,260,169 | B2 | 3/2022 | Estes |
| D954,078 | S | 6/2022 | Rahate et al. |

(56) References Cited

U.S. PATENT DOCUMENTS

| | | | |
|---|---|---|---|
| 2001/0016710 | A1 | 8/2001 | Nason et al. |
| 2001/0021803 | A1 | 9/2001 | Blank et al. |
| 2001/0034023 | A1 | 10/2001 | Stanton et al. |
| 2001/0034502 | A1 | 10/2001 | Moberg et al. |
| 2001/0048969 | A1 | 12/2001 | Constantino et al. |
| 2001/0051377 | A1 | 12/2001 | Hammer et al. |
| 2001/0053895 | A1 | 12/2001 | Vaillancourt |
| 2001/0056258 | A1 | 12/2001 | Evans |
| 2002/0010401 | A1 | 1/2002 | Bushmakin et al. |
| 2002/0010423 | A1 | 1/2002 | Gross et al. |
| 2002/0016568 | A1 | 2/2002 | Lebel et al. |
| 2002/0029018 | A1 | 3/2002 | Jeffrey |
| 2002/0032374 | A1 | 3/2002 | Holker et al. |
| 2002/0037221 | A1 | 3/2002 | Mastrangelo et al. |
| 2002/0040208 | A1 | 4/2002 | Flaherty et al. |
| 2002/0047768 | A1 | 4/2002 | Duffy |
| 2002/0066715 | A1 | 6/2002 | Niedospial |
| 2002/0070983 | A1 | 6/2002 | Kozub et al. |
| 2002/0123740 | A1 | 9/2002 | Flaherty et al. |
| 2002/0128543 | A1 | 9/2002 | Leonhardt |
| 2002/0147423 | A1 | 10/2002 | Burbank et al. |
| 2002/0155425 | A1 | 10/2002 | Han et al. |
| 2002/0161288 | A1 | 10/2002 | Shin et al. |
| 2002/0173769 | A1 | 11/2002 | Gray et al. |
| 2002/0173830 | A1 | 11/2002 | Starkweather et al. |
| 2002/0190818 | A1 | 12/2002 | Endou et al. |
| 2003/0023148 | A1 | 1/2003 | Lorenz et al. |
| 2003/0023152 | A1 | 1/2003 | Abbink et al. |
| 2003/0034124 | A1 | 2/2003 | Sugaya et al. |
| 2003/0040715 | A1 | 2/2003 | D'Antonio et al. |
| 2003/0050621 | A1 | 3/2003 | Lebel et al. |
| 2003/0055380 | A1 | 3/2003 | Flaherty |
| 2003/0060692 | A1 | 3/2003 | L. Ruchti et al. |
| 2003/0086073 | A1 | 5/2003 | Braig et al. |
| 2003/0086074 | A1 | 5/2003 | Braig et al. |
| 2003/0086075 | A1 | 5/2003 | Braig et al. |
| 2003/0090649 | A1 | 5/2003 | Sterling et al. |
| 2003/0097092 | A1 | 5/2003 | Flaherty |
| 2003/0100040 | A1 | 5/2003 | Bonnecaze et al. |
| 2003/0109827 | A1 | 6/2003 | Lavi et al. |
| 2003/0122647 | A1 | 7/2003 | Ou |
| 2003/0130616 | A1 | 7/2003 | Steil et al. |
| 2003/0135388 | A1 | 7/2003 | Martucci et al. |
| 2003/0144582 | A1 | 7/2003 | Cohen et al. |
| 2003/0148024 | A1 | 8/2003 | Kodas et al. |
| 2003/0163097 | A1 | 8/2003 | Fleury et al. |
| 2003/0170436 | A1 | 9/2003 | Sumi et al. |
| 2003/0175806 | A1 | 9/2003 | Rule et al. |
| 2003/0195404 | A1 | 10/2003 | Knobbe et al. |
| 2003/0198558 | A1 | 10/2003 | Nason et al. |
| 2003/0199825 | A1 | 10/2003 | Flaherty |
| 2003/0208113 | A1 | 11/2003 | Mault et al. |
| 2003/0208154 | A1 | 11/2003 | Close et al. |
| 2003/0212379 | A1 | 11/2003 | Bylund et al. |
| 2003/0216627 | A1 | 11/2003 | Lorenz et al. |
| 2003/0220605 | A1 | 11/2003 | Bowman et al. |
| 2003/0221621 | A1 | 12/2003 | Pokharna et al. |
| 2004/0001027 | A1 | 1/2004 | Killen et al. |
| 2004/0010207 | A1 | 1/2004 | Flaherty et al. |
| 2004/0034295 | A1 | 2/2004 | Salganicoff |
| 2004/0045879 | A1 | 3/2004 | Shults et al. |
| 2004/0051368 | A1 | 3/2004 | Caputo et al. |
| 2004/0064088 | A1 | 4/2004 | Gorman et al. |
| 2004/0064259 | A1 | 4/2004 | Haaland et al. |
| 2004/0068224 | A1 | 4/2004 | Couvillon et al. |
| 2004/0069004 | A1 | 4/2004 | Gist et al. |
| 2004/0069044 | A1 | 4/2004 | Lavi et al. |
| 2004/0087904 | A1 | 5/2004 | Langley et al. |
| 2004/0088224 | A1 | 5/2004 | Mukai |
| 2004/0092865 | A1 | 5/2004 | Flaherty et al. |
| 2004/0094733 | A1 | 5/2004 | Hower et al. |
| 2004/0097796 | A1 | 5/2004 | Berman et al. |
| 2004/0115068 | A1 | 6/2004 | Hansen et al. |
| 2004/0116847 | A1 | 6/2004 | Wall |
| 2004/0122353 | A1 | 6/2004 | Shahmirian et al. |
| 2004/0133166 | A1 | 7/2004 | Moberg et al. |
| 2004/0147034 | A1 | 7/2004 | Gore et al. |
| 2004/0153032 | A1 | 8/2004 | Garribotto et al. |
| 2004/0158208 | A1 | 8/2004 | Hiejima |
| 2004/0160437 | A1 | 8/2004 | Onozawa et al. |
| 2004/0171983 | A1 | 9/2004 | Sparks et al. |
| 2004/0203357 | A1 | 10/2004 | Nassimi |
| 2004/0204868 | A1 | 10/2004 | Maynard et al. |
| 2004/0215492 | A1 | 10/2004 | Choi |
| 2004/0220517 | A1 | 11/2004 | Starkweather et al. |
| 2004/0241736 | A1 | 12/2004 | Hendee et al. |
| 2004/0249308 | A1 | 12/2004 | Forssell |
| 2005/0003470 | A1 | 1/2005 | Nelson et al. |
| 2005/0020980 | A1 | 1/2005 | Inoue et al. |
| 2005/0022274 | A1 | 1/2005 | Campbell et al. |
| 2005/0033148 | A1 | 2/2005 | Haueter et al. |
| 2005/0049179 | A1 | 3/2005 | Davidson et al. |
| 2005/0065464 | A1 | 3/2005 | Talbot et al. |
| 2005/0065465 | A1 | 3/2005 | Lebel et al. |
| 2005/0075624 | A1 | 4/2005 | Miesel |
| 2005/0105095 | A1 | 5/2005 | Pesach et al. |
| 2005/0134609 | A1 | 6/2005 | Yu |
| 2005/0137573 | A1 | 6/2005 | Mclaughlin |
| 2005/0165363 | A1 | 7/2005 | Judson et al. |
| 2005/0171503 | A1 | 8/2005 | Van et al. |
| 2005/0182306 | A1 | 8/2005 | Sloan |
| 2005/0182366 | A1 | 8/2005 | Vogt et al. |
| 2005/0187524 | A1 | 8/2005 | Willis et al. |
| 2005/0192494 | A1 | 9/2005 | Ginsberg |
| 2005/0192557 | A1 | 9/2005 | Brauker et al. |
| 2005/0197621 | A1 | 9/2005 | Poulsen et al. |
| 2005/0203360 | A1 | 9/2005 | Brauker et al. |
| 2005/0203461 | A1 | 9/2005 | Flaherty et al. |
| 2005/0238507 | A1 | 10/2005 | Diianni et al. |
| 2005/0258581 | A1 | 11/2005 | Tanaka |
| 2005/0261660 | A1 | 11/2005 | Choi |
| 2005/0262451 | A1 | 11/2005 | Remignanti et al. |
| 2005/0272640 | A1 | 12/2005 | Doyle et al. |
| 2005/0273059 | A1 | 12/2005 | Mernoe et al. |
| 2005/0277882 | A1 | 12/2005 | Kriesel |
| 2005/0277912 | A1 | 12/2005 | John |
| 2006/0009727 | A1 | 1/2006 | O'Mahony et al. |
| 2006/0041229 | A1 | 2/2006 | Garibotto et al. |
| 2006/0064053 | A1 | 3/2006 | Bollish et al. |
| 2006/0079765 | A1 | 4/2006 | Neer et al. |
| 2006/0079809 | A1 | 4/2006 | Goldberger et al. |
| 2006/0086994 | A1 | 4/2006 | Viefers et al. |
| 2006/0100494 | A1 | 5/2006 | Kroll |
| 2006/0134323 | A1 | 6/2006 | O'Brien |
| 2006/0134491 | A1 | 6/2006 | Hilchenko et al. |
| 2006/0155210 | A1 | 7/2006 | Beckman et al. |
| 2006/0167350 | A1 | 7/2006 | Monfre et al. |
| 2006/0173406 | A1 | 8/2006 | Hayes et al. |
| 2006/0173439 | A1 | 8/2006 | Thorne et al. |
| 2006/0178633 | A1 | 8/2006 | Garibotto et al. |
| 2006/0189925 | A1 | 8/2006 | Gable et al. |
| 2006/0189926 | A1 | 8/2006 | Hall et al. |
| 2006/0197015 | A1 | 9/2006 | Sterling et al. |
| 2006/0200070 | A1 | 9/2006 | Callicoat et al. |
| 2006/0204535 | A1 | 9/2006 | Johnson |
| 2006/0229531 | A1 | 10/2006 | Goldberger et al. |
| 2006/0253085 | A1 | 11/2006 | Geismar et al. |
| 2006/0264895 | A1 | 11/2006 | Flanders |
| 2006/0270983 | A1 | 11/2006 | Lord et al. |
| 2006/0276771 | A1 | 12/2006 | Galley et al. |
| 2006/0282290 | A1 | 12/2006 | Flaherty et al. |
| 2007/0005018 | A1 | 1/2007 | Tekbuchava |
| 2007/0016127 | A1 | 1/2007 | Staib et al. |
| 2007/0025811 | A1 | 2/2007 | Wilhelm |
| 2007/0060796 | A1 | 3/2007 | Kim |
| 2007/0060869 | A1 | 3/2007 | Tolle et al. |
| 2007/0060872 | A1 | 3/2007 | Hall et al. |
| 2007/0073236 | A1 | 3/2007 | Mernoe et al. |
| 2007/0083160 | A1 | 4/2007 | Hall et al. |
| 2007/0088271 | A1 | 4/2007 | Richards |
| 2007/0100635 | A1 | 5/2007 | Mahajan et al. |
| 2007/0106135 | A1 | 5/2007 | Sloan et al. |
| 2007/0112332 | A1 | 5/2007 | Harding et al. |
| 2007/0116601 | A1 | 5/2007 | Patton |

(56) References Cited

U.S. PATENT DOCUMENTS

2007/0118405 A1 5/2007 Campbell et al.
2007/0129690 A1 6/2007 Rosenblatt et al.
2007/0142720 A1 6/2007 Ridder et al.
2007/0166453 A1 7/2007 Van et al.
2007/0173761 A1 7/2007 Kanderian et al.
2007/0173974 A1 7/2007 Lin
2007/0179352 A1 8/2007 Randlov et al.
2007/0191716 A1 8/2007 Goldberger et al.
2007/0197163 A1 8/2007 Robertson
2007/0225675 A1 9/2007 Robinson et al.
2007/0233019 A1 10/2007 Forsell
2007/0244381 A1 10/2007 Robinson et al.
2007/0249007 A1 10/2007 Rosero
2007/0259768 A1 11/2007 Kear et al.
2007/0264707 A1 11/2007 Liederman et al.
2007/0282269 A1 12/2007 Carter et al.
2007/0287985 A1 12/2007 Estes et al.
2007/0293843 A1 12/2007 Ireland et al.
2008/0004515 A1 1/2008 Jennewine
2008/0006500 A1 1/2008 Spahr
2008/0007141 A1 1/2008 Deck
2008/0033272 A1 2/2008 Gough et al.
2008/0033320 A1 2/2008 Racchini et al.
2008/0051738 A1 2/2008 Griffin
2008/0051764 A1 2/2008 Dent et al.
2008/0058625 A1 3/2008 Mcgarraugh et al.
2008/0065050 A1 3/2008 Sparks et al.
2008/0071157 A1 3/2008 Mcgarraugh et al.
2008/0071158 A1 3/2008 Mcgarraugh et al.
2008/0078400 A1 4/2008 Martens et al.
2008/0097289 A1 4/2008 Steil et al.
2008/0114304 A1 5/2008 Nalesso et al.
2008/0132880 A1 6/2008 Buchman
2008/0160492 A1 7/2008 Campbell et al.
2008/0161664 A1 7/2008 Mastrototaro et al.
2008/0172026 A1 7/2008 Blomquist
2008/0172028 A1 7/2008 Blomquist
2008/0177165 A1 7/2008 Blomquist et al.
2008/0183060 A1 7/2008 Steil et al.
2008/0188796 A1 8/2008 Steil et al.
2008/0200838 A1 8/2008 Goldberger et al.
2008/0206067 A1 8/2008 De et al.
2008/0208113 A1 8/2008 Damiano et al.
2008/0214919 A1 9/2008 Harmon et al.
2008/0228056 A1 9/2008 Blomquist et al.
2008/0243211 A1 10/2008 Cartwright et al.
2008/0249386 A1 10/2008 Besterman et al.
2008/0249508 A1 10/2008 Lopez et al.
2008/0269585 A1 10/2008 Ginsberg
2008/0269714 A1 10/2008 Mastrototaro et al.
2008/0269723 A1 10/2008 Mastrototaro et al.
2008/0287906 A1 11/2008 Burkholz et al.
2008/0294040 A1 11/2008 Mohiuddin et al.
2009/0006061 A1 1/2009 Thukral et al.
2009/0018406 A1 1/2009 Yodfat et al.
2009/0024083 A1 1/2009 Kriesel et al.
2009/0030398 A1 1/2009 Yodfat et al.
2009/0036753 A1 2/2009 King
2009/0043240 A1 2/2009 Robinson et al.
2009/0054753 A1 2/2009 Robinson et al.
2009/0054866 A1 2/2009 Teisen-Simony et al.
2009/0062767 A1 3/2009 Van et al.
2009/0069743 A1 3/2009 Krishnamoorthy et al.
2009/0069745 A1 3/2009 Estes et al.
2009/0069787 A1 3/2009 Estes et al.
2009/0099521 A1 4/2009 Gravesen et al.
2009/0105573 A1 4/2009 Malecha
2009/0124979 A1 5/2009 Raymond et al.
2009/0124994 A1 5/2009 Roe
2009/0131861 A1 5/2009 Braig et al.
2009/0156922 A1 6/2009 Goldberger et al.
2009/0156924 A1 6/2009 Shariati et al.
2009/0163781 A1 6/2009 Say et al.
2009/0198215 A1 8/2009 Chong et al.
2009/0198350 A1 8/2009 Thiele
2009/0212966 A1 8/2009 Panduro
2009/0221890 A1 9/2009 Saffer et al.
2009/0228214 A1 9/2009 Say et al.
2009/0278875 A1 11/2009 Holm et al.
2009/0299300 A1 12/2009 Truitt et al.
2009/0318791 A1 12/2009 Kaastrup
2009/0326343 A1 12/2009 Gable et al.
2009/0326472 A1 12/2009 Carter et al.
2010/0017141 A1 1/2010 Campbell et al.
2010/0036326 A1 2/2010 Matusch
2010/0057042 A1 3/2010 Hayter
2010/0064243 A1 3/2010 Buck et al.
2010/0077198 A1 3/2010 Buck et al.
2010/0114026 A1 5/2010 Karratt et al.
2010/0121170 A1 5/2010 Rule
2010/0137784 A1 6/2010 Cefai et al.
2010/0145272 A1 6/2010 Cefai et al.
2010/0152658 A1 6/2010 Hanson et al.
2010/0174228 A1 7/2010 Buckingham et al.
2010/0185183 A1 7/2010 Alme et al.
2010/0211003 A1 8/2010 Sundar et al.
2010/0228110 A1 9/2010 Tsoukalis
2010/0241066 A1 9/2010 Hansen et al.
2010/0241086 A1 9/2010 Yodfat et al.
2010/0262117 A1 10/2010 Magni et al.
2010/0262434 A1 10/2010 Shaya
2010/0295686 A1 11/2010 Sloan et al.
2010/0298765 A1 11/2010 Budiman et al.
2011/0021584 A1 1/2011 Berggren et al.
2011/0028817 A1 2/2011 Jin et al.
2011/0049394 A1 3/2011 De Rochemont
2011/0054390 A1 3/2011 Searle et al.
2011/0054399 A1 3/2011 Chong et al.
2011/0065224 A1 3/2011 Bollman et al.
2011/0071765 A1 3/2011 Yodfat et al.
2011/0073620 A1 3/2011 Verrilli
2011/0124996 A1 5/2011 Reinke et al.
2011/0144586 A1 6/2011 Michaud et al.
2011/0160652 A1 6/2011 Yodfat et al.
2011/0166512 A1 7/2011 Both et al.
2011/0178472 A1 7/2011 Cabiri
2011/0180480 A1 7/2011 Kloeffel et al.
2011/0190694 A1 8/2011 Lanier et al.
2011/0202005 A1 8/2011 Yodfat et al.
2011/0213329 A1 9/2011 Yodfat et al.
2011/0218495 A1 9/2011 Remde
2011/0230833 A1 9/2011 Landman et al.
2011/0251509 A1 10/2011 Beyhan et al.
2011/0313680 A1 12/2011 Doyle et al.
2011/0316562 A1 12/2011 Cefai et al.
2012/0003093 A1 1/2012 Lischer et al.
2012/0003935 A1 1/2012 Lydon et al.
2012/0010594 A1 1/2012 Holt et al.
2012/0030393 A1 2/2012 Ganesh et al.
2012/0053556 A1 3/2012 Lee
2012/0078067 A1 3/2012 Kovatchev et al.
2012/0078161 A1 3/2012 Masterson et al.
2012/0078181 A1 3/2012 Smith et al.
2012/0101451 A1 4/2012 Boit et al.
2012/0109066 A1 5/2012 Chase et al.
2012/0118138 A1 5/2012 Navarro et al.
2012/0123234 A1 5/2012 Atlas et al.
2012/0124521 A1 5/2012 Guo
2012/0136336 A1 5/2012 Mastrototaro et al.
2012/0150446 A1 6/2012 Chang et al.
2012/0172817 A1 7/2012 Brueggemann et al.
2012/0190955 A1 7/2012 Rao et al.
2012/0203085 A1 8/2012 Rebec
2012/0203178 A1 8/2012 Tverskoy
2012/0209207 A1 8/2012 Gray et al.
2012/0215087 A1 8/2012 Cobelli et al.
2012/0225134 A1 9/2012 Komorowski
2012/0226259 A1 9/2012 Yodfat et al.
2012/0232520 A1 9/2012 Sloan et al.
2012/0238851 A1 9/2012 Kamen et al.
2012/0250449 A1 10/2012 Nakano
2012/0271655 A1 10/2012 Knobel et al.
2012/0277668 A1 11/2012 Chawla
2012/0282111 A1 11/2012 Nip et al.

(56) References Cited

U.S. PATENT DOCUMENTS

| | | | |
|---|---|---|---|
| 2012/0295550 | A1 | 11/2012 | Wilson et al. |
| 2013/0006213 | A1 | 1/2013 | Arnitz et al. |
| 2013/0017099 | A1 | 1/2013 | Genoud et al. |
| 2013/0030358 | A1 | 1/2013 | Yodfat et al. |
| 2013/0060233 | A1 | 3/2013 | O'Connor et al. |
| 2013/0064701 | A1 | 3/2013 | Konishi |
| 2013/0158503 | A1 | 6/2013 | Kanderian et al. |
| 2013/0172695 | A1 | 7/2013 | Nielsen et al. |
| 2013/0172710 | A1 | 7/2013 | Mears et al. |
| 2013/0177455 | A1 | 7/2013 | Kamen et al. |
| 2013/0178791 | A1 | 7/2013 | Javitt |
| 2013/0178803 | A1 | 7/2013 | Raab |
| 2013/0231642 | A1 | 9/2013 | Doyle et al. |
| 2013/0245545 | A1 | 9/2013 | Arnold et al. |
| 2013/0253472 | A1 | 9/2013 | Cabiri |
| 2013/0261406 | A1 | 10/2013 | Rebec et al. |
| 2013/0267932 | A1 | 10/2013 | Franke et al. |
| 2013/0296792 | A1 | 11/2013 | Cabiri |
| 2013/0296823 | A1 | 11/2013 | Melker et al. |
| 2013/0298080 | A1 | 11/2013 | Griffin et al. |
| 2013/0317753 | A1 | 11/2013 | Kamen et al. |
| 2013/0332874 | A1 | 12/2013 | Rosinko et al. |
| 2013/0338576 | A1 | 12/2013 | O'Connor et al. |
| 2013/0346858 | A1 | 12/2013 | Neyrinck |
| 2014/0005633 | A1 | 1/2014 | Finan |
| 2014/0018730 | A1 | 1/2014 | Stephan |
| 2014/0032549 | A1 | 1/2014 | Mcdaniel et al. |
| 2014/0066859 | A1 | 3/2014 | Ogawa et al. |
| 2014/0066886 | A1 | 3/2014 | Roy et al. |
| 2014/0074033 | A1 | 3/2014 | Sonderegger et al. |
| 2014/0088428 | A1 | 3/2014 | Yang et al. |
| 2014/0108046 | A1 | 4/2014 | Echeverria et al. |
| 2014/0121635 | A1 | 5/2014 | Hayter |
| 2014/0127048 | A1 | 5/2014 | Diianni et al. |
| 2014/0128839 | A1 | 5/2014 | Diianni et al. |
| 2014/0129951 | A1 | 5/2014 | Amin et al. |
| 2014/0135880 | A1 | 5/2014 | Baumgartner et al. |
| 2014/0142508 | A1 | 5/2014 | Diianni et al. |
| 2014/0146202 | A1 | 5/2014 | Boss et al. |
| 2014/0148784 | A1 | 5/2014 | Anderson et al. |
| 2014/0171901 | A1 | 6/2014 | Langsdorf et al. |
| 2014/0180203 | A1 | 6/2014 | Budiman et al. |
| 2014/0180240 | A1 | 6/2014 | Finan et al. |
| 2014/0200426 | A1 | 7/2014 | Taub et al. |
| 2014/0200559 | A1 | 7/2014 | Doyle et al. |
| 2014/0230021 | A1 | 8/2014 | Birtwhistle et al. |
| 2014/0276554 | A1 | 9/2014 | Finan et al. |
| 2014/0276556 | A1 | 9/2014 | Saint et al. |
| 2014/0278123 | A1 | 9/2014 | Prodhom et al. |
| 2014/0309615 | A1 | 10/2014 | Mazlish |
| 2014/0316379 | A1 | 10/2014 | Sonderegger et al. |
| 2014/0325065 | A1 | 10/2014 | Birtwhistle et al. |
| 2015/0018633 | A1 | 1/2015 | Kovachev et al. |
| 2015/0025329 | A1 | 1/2015 | Amarasingham et al. |
| 2015/0025495 | A1 | 1/2015 | Peyser |
| 2015/0025503 | A1 | 1/2015 | Searle et al. |
| 2015/0041498 | A1 | 2/2015 | Kakiuchi et al. |
| 2015/0051487 | A1 | 2/2015 | Uber et al. |
| 2015/0057613 | A1 | 2/2015 | Clemente et al. |
| 2015/0064036 | A1 | 3/2015 | Eberhard |
| 2015/0120317 | A1 | 4/2015 | Mayou et al. |
| 2015/0134265 | A1 | 5/2015 | Kohlbrecher et al. |
| 2015/0134353 | A1 | 5/2015 | Ferrell et al. |
| 2015/0137017 | A1 | 5/2015 | Ambrosina et al. |
| 2015/0165119 | A1 | 6/2015 | Palerm et al. |
| 2015/0173674 | A1 | 6/2015 | Hayes et al. |
| 2015/0193585 | A1 | 7/2015 | Sunna |
| 2015/0202386 | A1 | 7/2015 | Brady et al. |
| 2015/0205509 | A1 | 7/2015 | Scriven et al. |
| 2015/0205511 | A1 | 7/2015 | Vinna et al. |
| 2015/0213217 | A1 | 7/2015 | Amarasingham et al. |
| 2015/0217052 | A1 | 8/2015 | Keenan et al. |
| 2015/0217053 | A1 | 8/2015 | Booth et al. |
| 2015/0265767 | A1 | 9/2015 | Vazquez et al. |
| 2015/0290389 | A1 | 10/2015 | Nessel |
| 2015/0297825 | A1 | 10/2015 | Focht et al. |
| 2015/0301691 | A1 | 10/2015 | Qin |
| 2015/0306314 | A1 | 10/2015 | Doyle et al. |
| 2015/0331995 | A1 | 11/2015 | Zhao et al. |
| 2015/0351671 | A1 | 12/2015 | Vanslyke et al. |
| 2015/0351672 | A1 | 12/2015 | Vanslyke et al. |
| 2015/0356250 | A1 | 12/2015 | Polimeni |
| 2015/0366945 | A1 | 12/2015 | Greene |
| 2016/0000999 | A1 | 1/2016 | Focht et al. |
| 2016/0008549 | A1 | 1/2016 | Plumptre et al. |
| 2016/0015891 | A1 | 1/2016 | Papiorek |
| 2016/0019352 | A1 | 1/2016 | Cohen et al. |
| 2016/0025544 | A1 | 1/2016 | Kamen et al. |
| 2016/0038673 | A1 | 2/2016 | Morales |
| 2016/0038689 | A1 | 2/2016 | Lee et al. |
| 2016/0051749 | A1 | 2/2016 | Istoc |
| 2016/0055842 | A1 | 2/2016 | Defranks et al. |
| 2016/0082187 | A1 | 3/2016 | Schaible et al. |
| 2016/0082242 | A1 | 3/2016 | Burton et al. |
| 2016/0089494 | A1 | 3/2016 | Guerrini |
| 2016/0129190 | A1 | 5/2016 | Haitsuka |
| 2016/0175520 | A1 | 6/2016 | Palerm et al. |
| 2016/0193423 | A1 | 7/2016 | Bilton |
| 2016/0213851 | A1 | 7/2016 | Weibel et al. |
| 2016/0220181 | A1 | 8/2016 | Rigoard et al. |
| 2016/0228641 | A1 | 8/2016 | Gescheit et al. |
| 2016/0243318 | A1 | 8/2016 | Despa et al. |
| 2016/0256087 | A1 | 9/2016 | Doyle et al. |
| 2016/0259889 | A1 | 9/2016 | Murtha et al. |
| 2016/0287512 | A1 | 10/2016 | Cooper et al. |
| 2016/0302054 | A1 | 10/2016 | Kimura et al. |
| 2016/0317741 | A1 | 11/2016 | List |
| 2016/0331310 | A1 | 11/2016 | Kovatchev |
| 2016/0354543 | A1 | 12/2016 | Cinar et al. |
| 2017/0007882 | A1 | 1/2017 | Werner |
| 2017/0021096 | A1 | 1/2017 | Cole et al. |
| 2017/0021137 | A1 | 1/2017 | Cole |
| 2017/0049386 | A1 | 2/2017 | Abraham et al. |
| 2017/0100541 | A1 | 4/2017 | Constantineau et al. |
| 2017/0128664 | A1 | 5/2017 | Diianni et al. |
| 2017/0131887 | A1 | 5/2017 | Kim et al. |
| 2017/0143899 | A1 | 5/2017 | Gondhalekar et al. |
| 2017/0143900 | A1 | 5/2017 | Rioux et al. |
| 2017/0156682 | A1 | 6/2017 | Doyle et al. |
| 2017/0173261 | A1 | 6/2017 | O'Connor et al. |
| 2017/0184091 | A1 | 6/2017 | Focht et al. |
| 2017/0188943 | A1 | 7/2017 | Braig et al. |
| 2017/0189625 | A1 | 7/2017 | Cirillo et al. |
| 2017/0216516 | A1 | 8/2017 | Dale et al. |
| 2017/0216524 | A1 | 8/2017 | Haider et al. |
| 2017/0239415 | A1 | 8/2017 | Hwang et al. |
| 2017/0258987 | A1 | 9/2017 | Caspers |
| 2017/0281877 | A1 | 10/2017 | Marlin et al. |
| 2017/0290975 | A1 | 10/2017 | Barmaimon et al. |
| 2017/0296746 | A1 | 10/2017 | Chen et al. |
| 2017/0311903 | A1 | 11/2017 | Davis et al. |
| 2017/0347971 | A1 | 12/2017 | Davis et al. |
| 2017/0348482 | A1 | 12/2017 | Duke et al. |
| 2018/0021521 | A1 | 1/2018 | Sanchez |
| 2018/0036495 | A1 | 2/2018 | Searle et al. |
| 2018/0040255 | A1 | 2/2018 | Freeman et al. |
| 2018/0075200 | A1 | 3/2018 | Davis et al. |
| 2018/0075201 | A1 | 3/2018 | Davis et al. |
| 2018/0075202 | A1 | 3/2018 | Davis et al. |
| 2018/0092576 | A1 | 4/2018 | Afonso |
| 2018/0126073 | A1 | 5/2018 | Wu et al. |
| 2018/0169334 | A1 | 6/2018 | Grosman et al. |
| 2018/0185579 | A1 | 7/2018 | Joseph et al. |
| 2018/0200434 | A1 | 7/2018 | Mazlish et al. |
| 2018/0200438 | A1 | 7/2018 | Mazlish et al. |
| 2018/0200441 | A1 | 7/2018 | Desborough et al. |
| 2018/0204636 | A1 | 7/2018 | Edwards et al. |
| 2018/0277253 | A1 | 9/2018 | Gondhalekar et al. |
| 2018/0289891 | A1 | 10/2018 | Finan et al. |
| 2018/0296757 | A1 | 10/2018 | Finan et al. |
| 2018/0307515 | A1 | 10/2018 | Meller et al. |
| 2018/0313346 | A1 | 11/2018 | Oakes et al. |
| 2018/0318499 | A1 | 11/2018 | Oakes et al. |
| 2018/0342317 | A1 | 11/2018 | Skirble et al. |

(56) References Cited

U.S. PATENT DOCUMENTS

| | | | |
|---|---|---|---|
| 2018/0369479 | A1 | 12/2018 | Hayter et al. |
| 2019/0076600 | A1 | 3/2019 | Grosman et al. |
| 2019/0095052 | A1 | 3/2019 | De et al. |
| 2019/0132801 | A1 | 5/2019 | Kamath et al. |
| 2019/0151547 | A1 | 5/2019 | Cowe et al. |
| 2019/0184091 | A1 | 6/2019 | Sjolund et al. |
| 2019/0192782 | A1 | 6/2019 | Pedersen et al. |
| 2019/0240403 | A1 | 8/2019 | Palerm et al. |
| 2019/0290844 | A1 | 9/2019 | Monirabbasi et al. |
| 2019/0321545 | A1 | 10/2019 | Saint |
| 2019/0336683 | A1 | 11/2019 | O'Connor et al. |
| 2019/0336684 | A1 | 11/2019 | O'Connor et al. |
| 2019/0348157 | A1 | 11/2019 | Booth et al. |
| 2019/0365993 | A1 | 12/2019 | Staub et al. |
| 2019/0374714 | A1 | 12/2019 | Rioux et al. |
| 2020/0001006 | A1 | 1/2020 | Pizzochero et al. |
| 2020/0009315 | A1 | 1/2020 | Brouet et al. |
| 2020/0046268 | A1 | 2/2020 | Patek et al. |
| 2020/0101222 | A1 | 4/2020 | Lintereur et al. |
| 2020/0101223 | A1 | 4/2020 | Lintereur et al. |
| 2020/0101225 | A1 | 4/2020 | O'Connor et al. |
| 2020/0113515 | A1 | 4/2020 | O'Connor et al. |
| 2020/0219625 | A1 | 7/2020 | Kahlbaugh |
| 2020/0342974 | A1 | 10/2020 | Chen et al. |
| 2020/0345931 | A1 | 11/2020 | Gray et al. |
| 2021/0050085 | A1 | 2/2021 | Hayter et al. |
| 2021/0098105 | A1 | 4/2021 | Lee et al. |
| 2022/0023536 | A1 | 1/2022 | Graham et al. |
| 2022/0105270 | A1 | 4/2022 | Doyle et al. |

FOREIGN PATENT DOCUMENTS

| | | | |
|---|---|---|---|
| CA | 606281 | A | 10/1960 |
| CA | 1040271 | A | 10/1978 |
| CA | 3026851 | A1 | 2/2020 |
| CN | 1297140 | A | 5/2001 |
| CN | 1375338 | A | 10/2002 |
| CN | 101208699 | A | 6/2008 |
| CN | 102498292 | A | 6/2012 |
| CN | 204972511 | U | 1/2016 |
| CN | 105764543 | A | 7/2016 |
| CN | 206175149 | U | 5/2017 |
| CN | 107096091 | A | 8/2017 |
| CN | 108472441 | A | 8/2018 |
| DE | 0420595 | C | 10/1925 |
| DE | 4200595 | A1 | 7/1993 |
| DE | 19723648 | C1 | 8/1998 |
| DE | 19756872 | A1 | 7/1999 |
| DE | 19920896 | A1 | 11/2000 |
| DE | 102005040344 | A1 | 3/2007 |
| EP | 0026056 | A1 | 4/1981 |
| EP | 0341049 | A2 | 11/1989 |
| EP | 0342947 | A2 | 11/1989 |
| EP | 0454331 | A1 | 10/1991 |
| EP | 0496305 | A2 | 7/1992 |
| EP | 0549341 | A1 | 6/1993 |
| EP | 0338806 | B1 | 2/1994 |
| EP | 0763369 | A1 | 3/1997 |
| EP | 0789146 | A1 | 8/1997 |
| EP | 0867196 | A2 | 9/1998 |
| EP | 0937475 | A2 | 8/1999 |
| EP | 0939451 | A1 | 9/1999 |
| EP | 1065378 | A2 | 1/2001 |
| EP | 1376759 | A2 | 1/2004 |
| EP | 1403519 | A1 | 3/2004 |
| EP | 1177802 | B1 | 9/2004 |
| EP | 1491144 | A1 | 12/2004 |
| EP | 1501573 | A2 | 2/2005 |
| EP | 1571582 | A2 | 9/2005 |
| EP | 0801578 | B1 | 7/2006 |
| EP | 1874390 | A2 | 1/2008 |
| EP | 2139382 | A1 | 1/2010 |
| EP | 2397181 | A1 | 12/2011 |
| EP | 2468338 | A1 | 6/2012 |
| EP | 2666520 | A1 | 11/2013 |
| EP | 2695573 | A2 | 2/2014 |
| EP | 2703024 | A1 | 3/2014 |
| EP | 2830499 | A1 | 2/2015 |
| EP | 2897071 | A1 | 7/2015 |
| EP | 2943149 | A1 | 11/2015 |
| EP | 3177344 | A1 | 6/2017 |
| EP | 3193979 | A1 | 7/2017 |
| EP | 3314548 | A1 | 5/2018 |
| EP | 3607985 | A1 | 2/2020 |
| FR | 2096275 | A5 | 2/1972 |
| FR | 2455269 | A1 | 11/1980 |
| FR | 2507637 | A1 | 12/1982 |
| FR | 2731475 | A1 | 9/1996 |
| GB | 0357139 | A | 9/1931 |
| GB | 0810488 | A | 3/1959 |
| GB | 0875034 | A | 8/1961 |
| GB | 1125897 | A | 9/1968 |
| GB | 1204836 | A | 9/1970 |
| GB | 2008806 | A | 6/1979 |
| GB | 2077367 | A | 12/1981 |
| GB | 2224444 | A | 5/1990 |
| GB | 2443261 | A | 4/2008 |
| GB | 2456681 | A | 7/2009 |
| GB | 2463051 | A | 3/2010 |
| GB | 2549750 | A | 11/2017 |
| IL | 46017 | A | 11/1977 |
| JP | 51-125993 | A | 11/1976 |
| JP | 02-131777 | A | 5/1990 |
| JP | 06-063133 | A | 3/1994 |
| JP | 06-296690 | A | 10/1994 |
| JP | 08-238324 | A | 9/1996 |
| JP | 2004-247271 | A | 9/2004 |
| JP | 2004-274719 | A | 9/2004 |
| JP | 2004-283378 | A | 10/2004 |
| JP | 2005-188355 | A | 7/2005 |
| JP | 2005-326943 | A | 11/2005 |
| JP | 2006-159228 | A | 6/2006 |
| JP | 2006-249130 | A | 9/2006 |
| JP | 2007-525276 | A | 9/2007 |
| JP | 2008-513142 | A | 5/2008 |
| JP | 2009-514580 | A | 4/2009 |
| JP | 2012-527981 | A | 11/2012 |
| JP | 6098988 | B2 | 3/2017 |
| JP | 2017-513577 | A | 6/2017 |
| JP | 2017-516548 | A | 6/2017 |
| JP | 2017-525451 | A | 9/2017 |
| JP | 2018-153569 | A | 10/2018 |
| JP | 2019-525276 | A | 9/2019 |
| NL | 1019126 | C1 | 4/2003 |
| TW | 200740148 | A | 10/2007 |
| TW | M452390 | U | 5/2013 |
| WO | 81/01658 | A1 | 6/1981 |
| WO | 86/06796 | A1 | 11/1986 |
| WO | 93/20864 | A1 | 10/1993 |
| WO | 94/15660 | A1 | 7/1994 |
| WO | 98/00193 | A1 | 1/1998 |
| WO | 98/01071 | A1 | 1/1998 |
| WO | 98/55073 | A1 | 12/1998 |
| WO | 98/56293 | A1 | 12/1998 |
| WO | 99/10040 | A1 | 3/1999 |
| WO | 99/10049 | A1 | 3/1999 |
| WO | 99/56803 | A1 | 11/1999 |
| WO | 99/62576 | A1 | 12/1999 |
| WO | 00/19887 | A1 | 4/2000 |
| WO | 00/29047 | A1 | 5/2000 |
| WO | 00/29049 | A1 | 5/2000 |
| WO | 00/30705 | A1 | 6/2000 |
| WO | 00/32258 | A1 | 6/2000 |
| WO | 00/48112 | A2 | 8/2000 |
| WO | 00/61215 | A1 | 10/2000 |
| WO | 00/74752 | A1 | 12/2000 |
| WO | 00/78210 | A1 | 12/2000 |
| WO | 01/05663 | A2 | 1/2001 |
| WO | 01/52727 | A1 | 7/2001 |
| WO | 01/56633 | A2 | 8/2001 |
| WO | 01/72354 | A2 | 10/2001 |
| WO | 01/76684 | A1 | 10/2001 |
| WO | 01/78812 | A1 | 10/2001 |
| WO | 02/15954 | A1 | 2/2002 |

(56) References Cited

FOREIGN PATENT DOCUMENTS

| | | | |
|---|---|---|---|
| WO | 02/20073 | A2 | 3/2002 |
| WO | 02/26282 | A2 | 4/2002 |
| WO | 02/40083 | A2 | 5/2002 |
| WO | 02/43866 | A2 | 6/2002 |
| WO | 02/68823 | A1 | 9/2002 |
| WO | 02/76535 | A1 | 10/2002 |
| WO | 02/82990 | A1 | 10/2002 |
| WO | 03/16882 | A1 | 2/2003 |
| WO | 03/30984 | A1 | 4/2003 |
| WO | 03/39362 | A1 | 5/2003 |
| WO | 03/45233 | A1 | 6/2003 |
| WO | 03/59420 | A1 | 7/2003 |
| WO | 03/90509 | A2 | 11/2003 |
| WO | 03/97133 | A1 | 11/2003 |
| WO | 2004/032994 | A2 | 4/2004 |
| WO | 2004/043250 | A1 | 5/2004 |
| WO | 2004/056412 | A2 | 7/2004 |
| WO | 2004/092715 | A1 | 10/2004 |
| WO | 2004/110526 | A1 | 12/2004 |
| WO | 2005/051170 | A2 | 6/2005 |
| WO | 2005/082436 | A1 | 9/2005 |
| WO | 2005/110601 | A1 | 11/2005 |
| WO | 2005/113036 | A1 | 12/2005 |
| WO | 2006/053007 | A2 | 5/2006 |
| WO | 2006/086201 | A2 | 8/2006 |
| WO | 2006/104806 | A2 | 10/2006 |
| WO | 2007/064835 | A2 | 6/2007 |
| WO | 2007/066152 | A2 | 6/2007 |
| WO | 2007/078937 | A2 | 7/2007 |
| WO | 2008/024810 | A2 | 2/2008 |
| WO | 2008/029403 | A1 | 3/2008 |
| WO | 2008/133702 | A1 | 11/2008 |
| WO | 2009/039203 | A2 | 3/2009 |
| WO | 2009/045462 | A1 | 4/2009 |
| WO | 2009/049252 | A1 | 4/2009 |
| WO | 2009/066287 | A2 | 5/2009 |
| WO | 2009/066288 | A1 | 5/2009 |
| WO | 2009/068251 | A1 | 6/2009 |
| WO | 2009/098648 | A2 | 8/2009 |
| WO | 2009/134380 | A2 | 11/2009 |
| WO | 2009/141005 | A1 | 11/2009 |
| WO | 2010/022069 | A2 | 2/2010 |
| WO | 2010/053702 | A1 | 5/2010 |
| WO | 2010/055504 | A1 | 5/2010 |
| WO | 2010/077279 | A1 | 7/2010 |
| WO | 2010/089418 | A2 | 8/2010 |
| WO | 2010/132077 | A1 | 11/2010 |
| WO | 2010/138848 | A1 | 12/2010 |
| WO | 2010/139793 | A1 | 12/2010 |
| WO | 2010/147659 | A2 | 12/2010 |
| WO | 2011/010198 | A2 | 1/2011 |
| WO | 2011/031458 | A1 | 3/2011 |
| WO | 2011/069935 | A2 | 6/2011 |
| WO | 2011/075042 | A1 | 6/2011 |
| WO | 2011/095483 | A1 | 8/2011 |
| WO | 2011/133823 | A1 | 10/2011 |
| WO | 2012/045667 | A2 | 4/2012 |
| WO | 2012/073032 | A1 | 6/2012 |
| WO | 2012/108959 | A1 | 8/2012 |
| WO | 2012/134588 | A1 | 10/2012 |
| WO | 2012/134589 | A1 | 10/2012 |
| WO | 2012/177353 | A1 | 12/2012 |
| WO | 2012/178134 | A2 | 12/2012 |
| WO | 2013/050535 | A2 | 4/2013 |
| WO | 2013/078200 | A1 | 5/2013 |
| WO | 2013/134486 | A2 | 9/2013 |
| WO | 2013/137893 | A1 | 9/2013 |
| WO | 2013/149186 | A1 | 10/2013 |
| WO | 2013/177565 | A1 | 11/2013 |
| WO | 2013/182321 | A1 | 12/2013 |
| WO | 2014/029416 | A1 | 2/2014 |
| WO | 2014/035672 | A2 | 3/2014 |
| WO | 2014/099404 | A1 | 6/2014 |
| WO | 2014/109898 | A1 | 7/2014 |
| WO | 2014/110538 | A1 | 7/2014 |
| WO | 2014/149357 | A1 | 9/2014 |
| WO | 2014/179774 | A1 | 11/2014 |
| WO | 2014/194183 | A2 | 12/2014 |
| WO | 2015/032772 | A1 | 3/2015 |
| WO | 2015/048791 | A1 | 4/2015 |
| WO | 2015/056259 | A1 | 4/2015 |
| WO | 2015/061493 | A1 | 4/2015 |
| WO | 2015/073211 | A1 | 5/2015 |
| WO | 2015/081337 | A2 | 6/2015 |
| WO | 2015/117082 | A1 | 8/2015 |
| WO | 2015/117854 | A1 | 8/2015 |
| WO | 2015/167201 | A1 | 11/2015 |
| WO | 2015/177082 | A1 | 11/2015 |
| WO | 2015/187366 | A1 | 12/2015 |
| WO | 2016/004088 | A1 | 1/2016 |
| WO | 2016/022650 | A1 | 2/2016 |
| WO | 2016/041873 | A1 | 3/2016 |
| WO | 2016/089702 | A1 | 6/2016 |
| WO | 2016/141082 | A1 | 9/2016 |
| WO | 2016/161254 | A1 | 10/2016 |
| WO | 2017/004278 | A1 | 1/2017 |
| WO | 2017/091624 | A1 | 6/2017 |
| WO | 2017/105600 | A1 | 6/2017 |
| WO | 2017/148855 | A1 | 9/2017 |
| WO | 2017/184988 | A1 | 10/2017 |
| WO | 2017/187177 | A1 | 11/2017 |
| WO | 2017/205816 | A1 | 11/2017 |
| WO | 2018/009614 | A1 | 1/2018 |
| WO | 2018/067748 | A1 | 4/2018 |
| WO | 2018/120104 | A1 | 7/2018 |
| WO | 2018/136799 | A1 | 7/2018 |
| WO | 2018/204568 | A1 | 11/2018 |
| WO | 2019/077482 | A1 | 4/2019 |
| WO | 2019/094440 | A1 | 5/2019 |
| WO | 2019/213493 | A1 | 11/2019 |
| WO | 2019/246381 | A1 | 12/2019 |
| WO | 2020/081393 | A1 | 4/2020 |
| WO | 2021/011738 | A1 | 1/2021 |
| WO | 2021/016452 | A1 | 1/2021 |

OTHER PUBLICATIONS

Invitation to Pay Additional Fees for International Application No. PCT/US2013/034674, mailed on Jun. 3, 2013, 2 pages.

Irby et al., "Optimization and Application of a Wrap-Spring Clutch to a Dynamic Knee-Ankle-Foot Orthosis", IEEE Transactions on Rehabilitation Engineering, vol. 7, No. 2, Jun. 1999, pp. 130-134.

Notice of Allowance dated Mar. 25, 2016, issued in U.S. Appl. No. 13/854,456, 9 pages.

Notice of Allowance dated May 21, 2018, issued in U.S. Appl. No. 13/854,463, 9 pages.

Notice of Allowance dated May 23, 2018, issued in U.S. Appl. No. 13/854,445, 8 pages.

Office Action dated May 31, 2016, issued in U.S. Appl. No. 13/854,463, 15 pages.

Schott web-page image from Jul. 9, 2016, https://www.US.schott.com/pharmaceutical_packaging/english/products/ cartrid es.html.

Sclater et al., "Mechanisms and Mechanical Devices Sourcebook", McGraw-Hill, 2001, 3rd Edition ISBN: 0-07-136169-3.

Sclater et al., "Mechanisms and Mechanical Devices Sourcebook", McGraw-Hill, 2011, 5th edition ISBN: 978-0-07-170441-0.

Second Affidavit of Peter P. Pott, Oct. 4, 2024.

Third Party Opposition by EOFlow Co., Ltd. Submitted in European Application No. 23152851.4, submission dated Mar. 26, 2025, 123 pages.

Third Party Opposition by Inspicos P/S Submitted in European Application No. 23152851.4, submission dated Mar. 26, 2025, 23 pages.

Third Party Opposition by Keller Schneider Patentanwalts GMBH Submitted in European Application No. 23152851.4, submission dated Mar. 26, 2025, 16 pages.

U.S. Office Action dated Aug. 4, 2015, issued in U.S. Appl. No. 13/854,463, 10 pages.

U.S. Office Action dated Jan. 25, 2017, issued in U.S. Appl. No. 13/854,445, 22 pages.

(56) References Cited

OTHER PUBLICATIONS

U.S. Office Action dated Mar. 3, 2017, issued in U.S. Appl. No. 13/854,463, 11 pages.
U.S. Office Action dated Mar. 31, 2015, issued in U.S. Appl. No. 13/854,456, 10 pages.
U.S. Office Action dated May 17, 2016, issued in U.S. Appl. No. 13/854,445, 10 pages.
U.S. Office Action dated May 31, 2016, issued in U.S. Appl. No. 13/854,463, 16 pages.
U.S. Office Action dated Oct. 31, 2017, issued in U.S. Appl. No. 13/854,445, 14 pages.
U.S. Office Action dated Oct. 31, 2017, issued in U.S. Appl. No. 13/854,463 13 pages.
U.S. Office Action dated Sep. 23, 2015, issued in U.S. Appl. No. 13/854,456, 13 pages.
User's Guide for Model 508 Insulin Pump, Mini Med, Aug. 2000, 145 pages.
Vaughan, M.E., ""The Design, Fabrication, and Modeling of a Piezoelectric Linear Motor."" Master's thesis, Virginia Polytechnic Institute and State University, VA. (2001).
Web-Site Brochure dated Dec. 20, 1999. "The Animas R-1000 Insulin Pump", www.animascorp.com/pump_f_ s.html.
Web-Site Brochure dated Dec. 20, 1999. Applied Medical Technology. "508 Pump Information", www.applied-medical. co.uk/508.htm.
Web-Site Brochure dated Jan. 4, 2000. "The Glucose Sensor".www.animascorp.corn/sensor_f.html.
Web-Site Brochure dated Jan. 4, 2000. MiniMed 508. "Doing its job. Naturally." www.minimed.com/files/mm113.htm.
Web-Site Brochure dated Jan. 4, 2000. SOOIL-Homepage. "Portable Insulin Pump", www.sooil.com/product2.htm.
"Lind, et al. "Linear Motion Miniature Actuators."" Paper presented at the 2nd Tampere International Conference on Machine Automation, Tampere, Finland (Sep. 1998), 12 pages.
Author unknown, "The Animas R-1000 Insulin Pump—Animas Corporation intends to exit the insulin pump business and discontinue the manufacturing and sale of Animas Vibe and One Touch Ping insulin pumps." [online], Dec. 1999 [retrieved on Jan. 8, 2019], Retrieved from the Internet URL: http://www.animaspatientsupport.com/ using the Wayback Machine.
Author unknown, CeramTec ""Discover the Electro Ceramic Products CeramTec acquired from Morgan AdvancedMaterials"" [online], Mar. 1, 2001 [retrieved on Jan. 8, 2019. Retrieved from the Internet URL: http://www.rnorgantechnicalceramics.com/.
Decision UPC Docket No. CFI_380/2024, Nov. 22, 2024.
Decision UPC Docket No. CFI_400/2024, Nov. 22, 2024.
Diianni et al., Fluid Delivery Device with Transcutaneous Access Tool, Insertion Mechanism and Blood Glucose Monitoring for Use Therewith, filed Feb. 19, 2019, European Patent Application No. 19157933.3 (the 1st divisional application), 54 pages.
EPO Search Report dated Nov. 11, 2015, received in corresponding Application No. 13768938.6, 7 pgs.
European Communication pursuant to Article 94(3) EPC for European Application No. 19157933.3, dated Apr. 30, 2020, 3 pages.
European Communication pursuant to Article 94(3) EPC for European Application No. 19157933.3, dated Mar. 18, 2021, 4 pages.
European Communication pursuant to Article 94(3) EPC for European Application No. 19157933.3, dated Oct. 1, 2021, 3 pages.
European Search Report and Written Opinion for the European Patent Application No. EP19177571, dated Oct. 30, 2019, 8 pages.
European Search Report and Written Opinion for the European Patent Application No. EP20174878, dated Sep. 29, 2020, 3 pages.
Extended European Search Report and Search Opinion Received for EP Application No. 19157933.3, dated on Jul. 2, 2019, 6 pages.
Extended European Search Report and Search Opinion Received for EP Application No. 23152851.4, dated on May 31, 2023, 7 pages.
Extended European Search Report and Search Opinion Received for EP Application No. 24181903.6, dated on Sep. 16, 2024, 7 pages.
First Affidavit of Peter P. Pott, Sep. 15, 2024.
Galante, et al., "Design, Modeling, and Performance of a High Force Piezoelectric Inchworm Motor," Journal of Intelligent Material Systems and Structures, vol. 10, 962-972 (1999).
International Preliminary Report on Patentability dated Apr. 9, 2020, issued in PCT Patent Application No. PCT/ US2018/052464, 7 pages.
International Preliminary Report on Patentability dated Oct. 1, 2014, issued in PCT Patent Application No. PCT/ US2013/034674, 15 pages.
International Preliminary Report on Patentability for International application No. PCT/US2017/034811 dated Nov. 27, 2018 10 pages.
International Preliminary Report on Patentability for the International Patent Application No. PCT/US18/14351, dated Jul. 23, 2019, 6 pages.
International Preliminary Report on Patentability for the International Patent Application No. PCT/US2017/046508 dated Feb. 12, 2019 10 pp.
International Preliminary Report on Patentability for the International Patent Application No. PCT/US2017/046737, dated Feb. 19, 2019, 8 pages.
International Preliminary Report on Patentability for the International Patent Application No. PCT/US2017/055054, dated Apr. 9, 2019, 8 pages.
International Preliminary Report on Patentability for the International Patent Application No. PCT/US2018/045155, dated Feb. 4, 2020, 10 pages.
International Preliminary Reporton Patentability for the International Patent Application No. PCT/US2017/046777, dated Feb. 19, 2019, 8 pages.
International Search Report and the Written Opinion of the International Searching Authority in PCT Application No. PCT/GB2015/050248, dated Jun. 23, 2015, 11 pages.
International Search Report and Written Opinion for application No. PCT/US18/52464, dated Jan. 4, 2019, 11 pages.
International Search Report and Written Opinion for application No. PCT/US2017/015601, dated May 16, 2017, 12 pages.
International Search Report and Written Opinion for application No. PCT/US2017/034811, dated Oct. 18, 2017, 15 pages.
International Search Report and Written Opinion for Application No. PCT/US2019/059854, dated Aug. 26, 2020, 10 pages.
International Search Report and Written Opinion for Interantional application No. PCT/US2017/055054, dated Jan. 25, 2018, 14 pages.
International Search Report and Written Opinion for International application No. PCT/GB2007/004073, dated Jan. 31, 2008, 8 pages.
International Search Report and Written Opinion for International application No. PCT/US2017/034814, dated Oct. 11, 2017, 16 pages.
International Search Report and Written Opinion for International application No. PCT/US2017/046508, dated Jan. 17, 2018, 14 pages.
International Search Report and Written Opinion for International application No. PCT/US2017/046737, dated Dec. 14, 2017, 11 pages.
International Search Report and Written Opinion for International application No. PCT/US2017/046777, dated Dec. 13, 2017, 14 pages.
International Search Report and Written Opinion for International application No. PCT/US2018/045155, dated Oct. 15, 2018, 12 pages.
International Search Report and Written Opinion for International Patent Application No. PCT/US2022/011356, dated Apr. 29, 2022, 17 pages.
International Search Report and Written Opinion for International Patent Application No. PCT/US2022/029012, mailed Aug. 19, 2022, 10 pages.
International Search Report and Written Opinion for PCT Application No. PCT/US2022/015985, dated May 30, 2022, 13 pages.
International Search Report and Written Opinion for PCT/US2018/014351, dated Jun. 4, 2018, 9 pages.
International Search Report and Written Opinion for the International Patent Application No. PCT/US2019/035756, datd Jul. 31, 2019, 11 pages.

(56) References Cited

OTHER PUBLICATIONS

International Search Report and Written Opinion for the International Patent Application No. PCT/US2019/063615, dated May 3, 2020, 13 pages.
International Search Report and Written Opinion for the International Patent Application No. PCT/US2021/055581, dated Feb. 8, 2022, 15 pages.
International Search Report and Written Opinion of PCT/US2018/018901, dated Aug. 6, 2018, 12 pages.
International Search Report and Written Opinion, Application No. PCT/US2022/016713, mailed Aug. 5, 2022, 19 pages.
International Search Report for International Application No. PCT/US2013/034674, mailed Aug. 6, 2013, 4 pages.
International Search Report for the International Patent Application No. PCT/US03/16640, dated Oct. 2, 2003, 1 page.
International Written Opinion for International Application No. PCT/US2013/034674, mailed Aug. 6, 2013, 13 pages.

* cited by examiner

FLUID DELIVERY DEVICE, TRANSCUTANEOUS ACCESS TOOL AND FLUID DRIVE MECHANISM FOR USE THEREWITH

CROSS-REFERENCE TO RELATED APPLICATIONS

This application is a continuation of U.S. patent application Ser. No. 17/580,913, filed Jan. 21, 2022, now U.S. Pat. No. 12,329,928, issued Jun. 17, 2025, which is a continuation of U.S. patent application Ser. No. 16/552,492, filed Aug. 27, 2019, now U.S. Pat. No. 11,229,741, issued Jan. 25, 2022, which is a continuation of U.S. patent application Ser. No. 15/226,510, filed Aug. 2, 2016, now U.S. Pat. No. 10,420,883, issued Sep. 24, 2019, which is a continuation of U.S. patent application Ser. No. 13/854,456, filed Apr. 1, 2013, now U.S. Pat. No. 9,402,950, issued Aug. 2, 2016, which is a continuation of PCT Application Ser. No. PCT/US2013/034674, filed Mar. 29, 2013 and claims the benefit of the filing date of U.S. Provisional Application Ser. No. 61/618,028, filed Mar. 30, 2012, the teachings of each of which are incorporated herein by reference.

TECHNICAL FIELD

The present invention relates to fluid delivery devices for delivering therapeutic liquids to a patient, and more particularly, to an infusion pump for delivering therapeutic liquids to a patient.

BACKGROUND

Fluid delivery devices have numerous uses such as delivering a liquid medicine or other therapeutic fluid to a patient subcutaneously. In a patient with diabetes mellitus, for example, ambulatory infusion pumps have been used to deliver insulin to a patient. These ambulatory infusion pumps have the ability to offer sophisticated fluid delivery profiles including variable basal rates and bolus requirements. The ability to carefully control drug delivery can result in better efficacy of the drug and therapy and less toxicity to the patient.

Some existing ambulatory infusion pumps include a reservoir to contain the liquid medicine and use electromechanical pumping or metering technology to deliver the liquid medicine via tubing to a needle and/or soft cannula that is inserted subcutaneously into the patient. These existing devices allow control and programming via electromechanical buttons or switches located on the housing of the device. The devices include visual feedback via text or graphic screens and may include alert or warning lights and audio or vibration signals and alarms. Such devices are typically worn in a harness or pocket or strapped to the body of the patient.

Some infusion pumps have been designed to be relatively small, low cost, light-weight, and easy-to-use. One example of such a pump is the OMNIPOD® insulin infusion pump available from Insulet Corporation. Examples of infusion pumps are also described in greater detail, for example, in U.S. Pat. Nos. 7,128,727; 7,018,360; and 7,144,384 and U.S. Patent Application Publication Nos. 2007/0118405, 2006/0282290, 2005/0238507, and 2004/0010207, which are fully incorporated herein by reference. These pumps include insertion mechanisms for causing a transcutaneous access tool, such as a needle and/or soft cannula, to be inserted into a patient. Although such pumps are effective and provide significant advantages over other insulin infusion pumps, the design of the insertion mechanism may be improved, for example, to reduce the size of the pump, to improve the comfort to the user, and/or to incorporate continuous glucose monitoring (CGM). These pumps also include fluid driving mechanisms for driving fluid from a reservoir through the transcutaneous access tool. The fluid driving mechanisms may also be improved to facilitate assembly and use of the pump.

BRIEF SUMMARY

The present disclosure provides various fluid delivery devices to deliver a liquid medicine or other therapeutic fluid to a patient subcutaneously. In certain embodiments the fluid delivery device may comprise an ambulatory insulin infusion device to administer insulin to a patient. The fluid delivery device may include one or more batteries for providing a power source, a fluid reservoir for holding a fluid, a fluid drive mechanism for driving the fluid out of the reservoir, a fluid passage mechanism for receiving the fluid from the reservoir and passing the fluid to a destination via a transcutaneous access tool, and a transcutaneous access tool insertion mechanism for deploying the transcutaneous access tool.

In certain embodiments, the drive mechanism may comprise a clutch mechanism. As explained herein, by using a clutch mechanism, the number of fluid path prime pulses to prime the pump may be reduced and a full and proper priming of the fluid path before placement on the body may be better assured. The clutch mechanism may also be made suitable for other drug applications without significant redesign, and be more easily inspected than conventional drive mechanisms for infusion devices.

In certain embodiments, the fluid delivery device may comprise a fluid reservoir; a transcutaneous access tool fluidly coupled to the fluid reservoir; and a drive mechanism for driving fluid from the reservoir. The drive mechanism may comprise a plunger received in the reservoir; a leadscrew extending from the plunger; a nut threadably engaged with the leadscrew; a drive wheel; and a clutch mechanism coupled to the drive wheel, wherein the clutch mechanism is configured to allow the nut to pass through the clutch mechanism when disengaged and is configured to grip the nut when engaged such that the drive wheel rotates the nut to advance the leadscrew and the plunger into the reservoir.

In certain embodiments, the fluid delivery device may comprise a fluid reservoir; a transcutaneous access tool fluidly coupled to the fluid reservoir; and a drive mechanism for driving fluid from the reservoir The drive mechanism may comprise a plunger received in the reservoir; an elongated assembly comprising a first elongated member and a second elongated member; the first elongated member extending from the plunger; the second elongated member coupled to the first elongated member; a drive wheel; and a clutch mechanism coupled to the drive wheel, wherein the clutch mechanism is configured to allow the second elongated member to pass through when disengaged and is configured to grip the second elongated member when engaged such that the drive wheel rotates the second elongated member to advance the first elongated member and the plunger into the reservoir.

In certain embodiments, a method of operating a foregoing fluid delivery device may comprise providing the fluid delivery device; holding the clutch mechanism in a disengaged position; filling the fluid reservoir with fluid; passing the second elongated member through the clutch mechanism such that the plunger is retracted within the reservoir; releasing the clutch mechanism from the disengaged position; and engaging the clutch mechanism with the second elongated member.

BRIEF DESCRIPTION OF THE DRAWINGS

These and other features and advantages will be better understood by reading the following detailed description, taken together with the drawings wherein.

DETAILED DESCRIPTION

Figure 1:
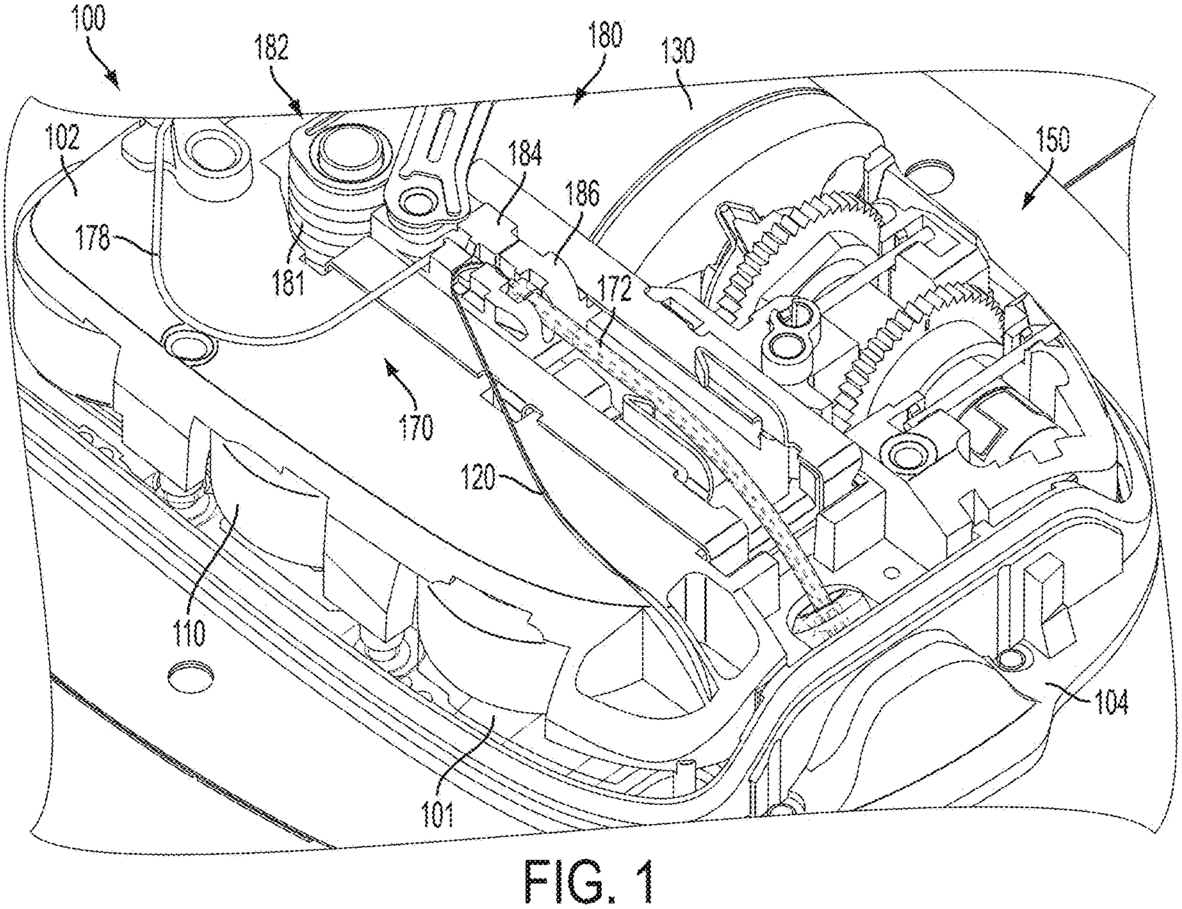
FIG. 1 is a top perspective view of a fluid delivery device with a transcutaneous access tool insertion mechanism in a pre-deployment position, consistent with the present disclosure.
Figure 2:
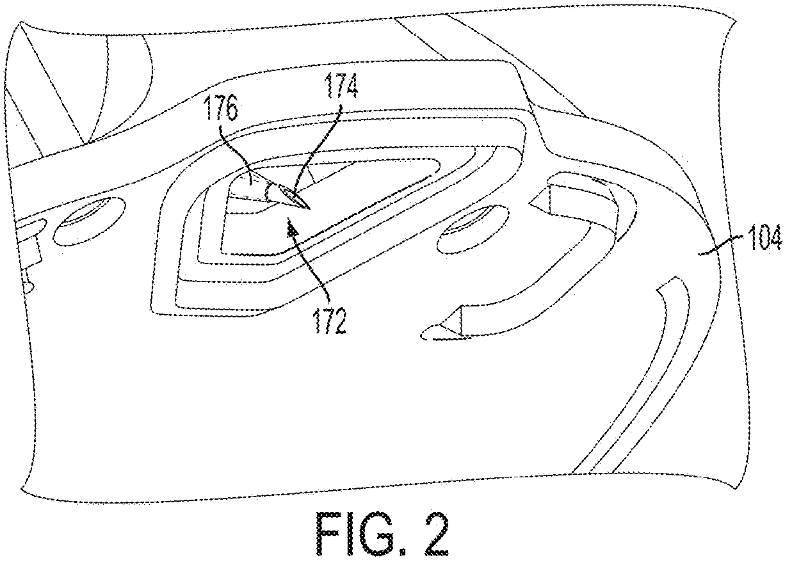
FIG. 2 is a bottom perspective view of a needle and cannula retracted into the fluid delivery device in the pre-deployment position shown in FIG. 1.
Figure 3:
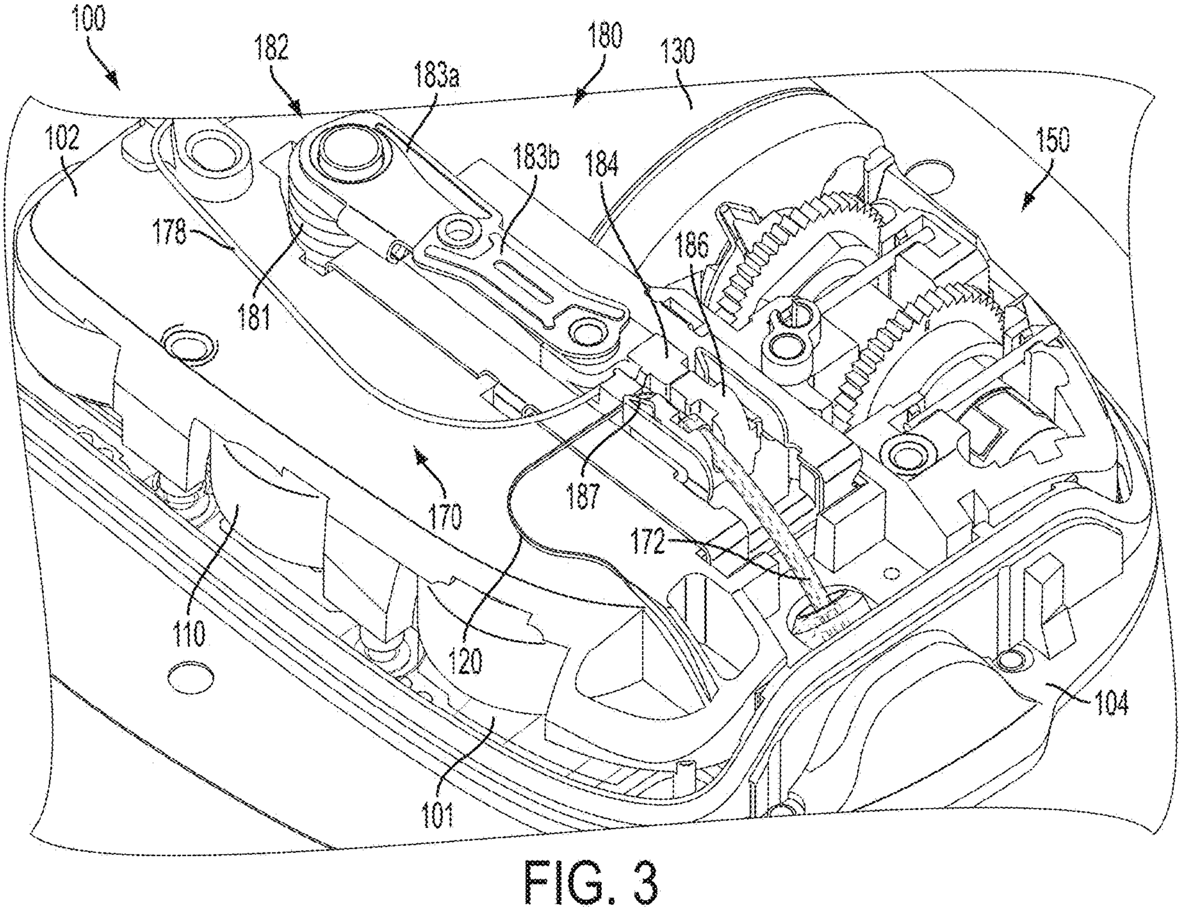
FIG. 3 is a top perspective view of the fluid delivery device shown in FIG. 1 with the insertion mechanism in an intermediate position.
Figure 4:
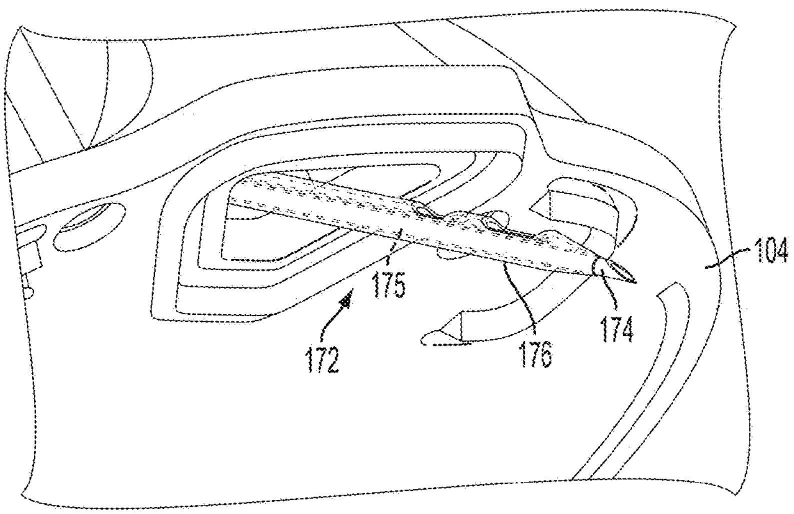
FIG. 4 is a bottom perspective view of the needle and cannula extending from the fluid delivery device in the intermediate position shown in FIG. 3.
Figure 5:
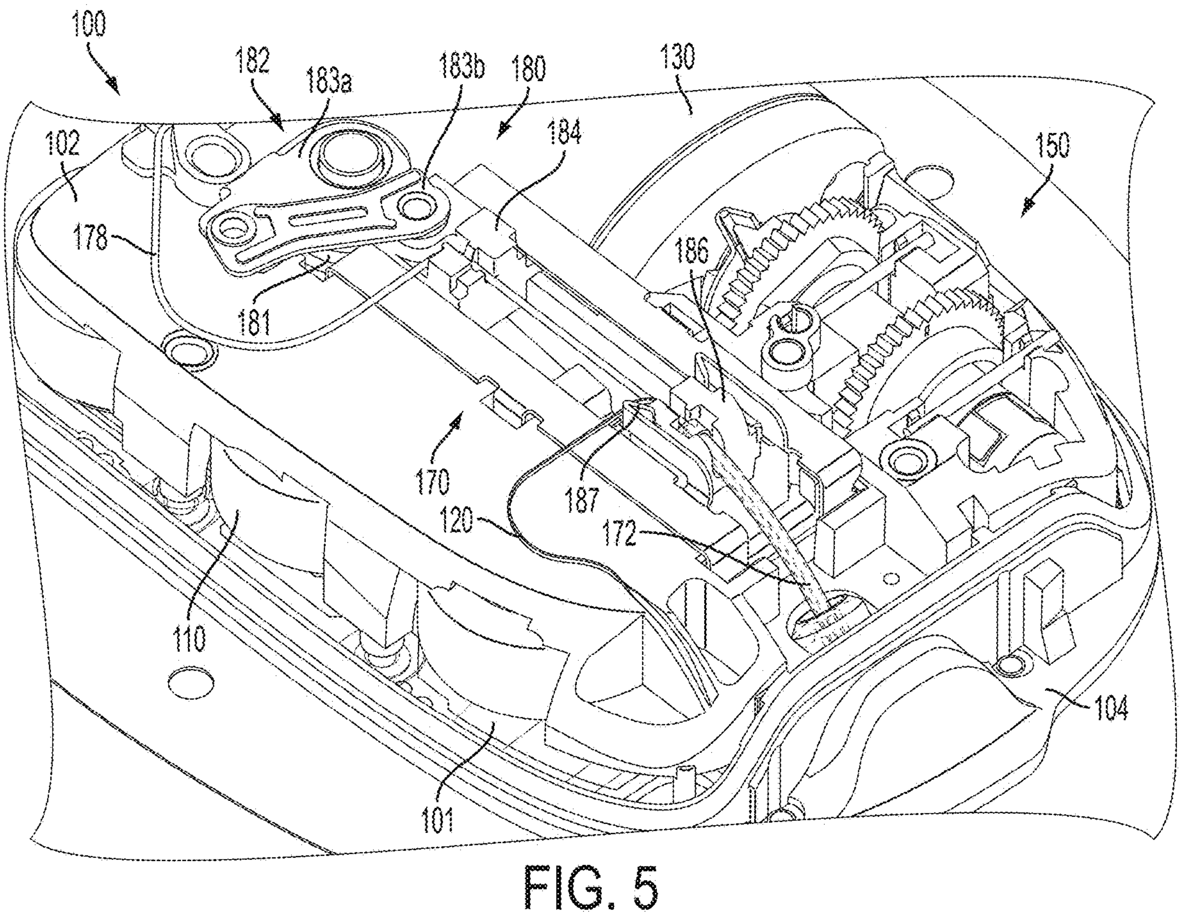
FIG. 5 is a top perspective view of the fluid delivery device shown in FIG. 1 with the insertion mechanism in a post-deployment position.

A fluid delivery device, consistent with embodiments of the present disclosure, may be used to deliver a therapeutic fluid (e.g., a liquid medicine) to a patient via a transcutaneous access tool, such as a needle/trocar and/or a cannula. A transcutaneous access tool insertion mechanism may be used to deploy the transcutaneous access tool, for example, by inserting and retracting a needle/trocar in a single, uninterrupted motion. The insertion mechanism may also provide an increasing insertion force as the needle/trocar moves in the insertion direction. The fluid delivery device may also include a clutch mechanism to facilitate filling a reservoir and engagement of a drive mechanism for driving fluid out of the reservoir. In certain embodiments, the fluid delivery device may comprise an ambulatory insulin infusion device.

In other embodiments, a fluid delivery device may be used to deliver a therapeutic fluid to a patient with integrated monitoring, such as continuous glucose monitoring (CGM). In these embodiments, the fluid deliver device may include a transcutaneous access tool configured to introduce a monitoring test strip through the skin of the patient, for example, using one or more needles, cannulas and/or trocars.

Referring to FIGS. 1-6, one embodiment of a fluid delivery device 100 is shown and described. In the exemplary embodiment, the fluid delivery device 100 is used to subcutaneously deliver a fluid, such as a liquid medicine (e.g., insulin), to a person or an animal. Those skilled in the art will recognize that the fluid delivery device 100 may be used to deliver other types of fluids. The fluid delivery device 100 may be used to deliver fluids in a controlled manner, for example, according to fluid delivery profiles accomplishing bolus requirements, continuous infusion and variable flow rate delivery.

According to one embodiment, the fluid delivery device 100 may include one or more batteries 110 for providing a power source, a fluid reservoir 130 for holding a fluid, a fluid drive mechanism 150 for driving the fluid out of the reservoir 130, a fluid passage mechanism 170 for receiving the fluid from the reservoir 130 and passing the fluid to a destination via a transcutaneous access tool 172, and a transcutaneous access tool insertion mechanism 180 for deploying the transcutaneous access tool 172. The fluid delivery device 100 may include a circuit board 101 with control circuitry for controlling the device and a chassis 102 that provides mechanical and/or electrical connections between components of the fluid delivery device 100. The fluid delivery device 100 may also include a housing 104 to enclose the circuit board 101, the chassis 102, and the components 110, 130, 150, 170, 180.

The fluid delivery device 100 may also include integrated monitoring such as continuous glucose monitoring (CGM). A monitor test strip 120 coupled to a monitor (not shown) in the fluid delivery device 100 may be introduced by the transcutaneous access tool 172 subcutaneously. One example of the monitor test strip is a CGM test strip (such as the type available from Nova Biomedical) which may be understood as a glucose sensor configured to test for a concentration level of glucose in the blood of a patient. The fluid delivery device 100 may be configured to receive data from the monitoring test strip concerning a glucose level of the patient, and determining an output of insulin from the reservoir based on the glucose level.

The transcutaneous access tool 172 includes an introducer needle/trocar 174 at least partially positioned within a lumen 175 of a cannula 176 (e.g., a soft flexible cannula), which is capable of passing the fluid into the patient. In particular, the introducer needle/trocar 174 may initially penetrate the skin such that both the introducer needle/trocar 174 and the cannula 176 are introduced (inserted) into the patient, and the introducer needle/trocar 174 may then be retracted within the cannula 176 such that the cannula 176 remains inserted. A fluid path, such as tubing 178, fluidly couples the reservoir 130 to the lumen 175 of cannula 176 of the transcutaneous access tool 172.

Figure 6:
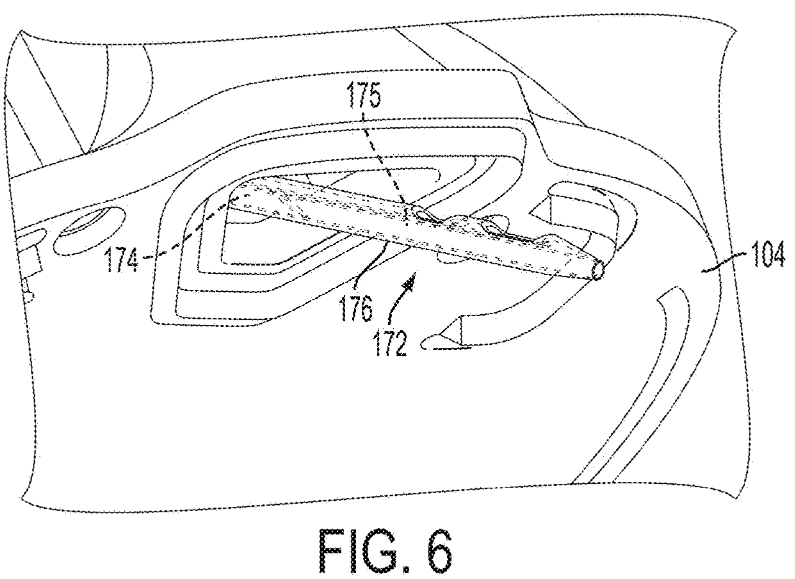
FIG. 6 is a bottom perspective view of the cannula extending from the fluid delivery device in the post-deployment position shown in FIG. 5.

The transcutaneous access tool insertion mechanism 180 is coupled to the transcutaneous access tool 172 to deploy the transcutaneous access tool 172, for example, by inserting the needle/trocar 174 and cannula 176 through the skin of a patient and retracting the needle/trocar 174. In the illustrated embodiment, the insertion mechanism 180 includes a spring-biased linkage mechanism 182 and sliding members 184, 186 coupled to the needle/trocar 174 and cannula 176, respectively, for moving the needle/trocar 174 and cannula 176 in the insertion direction and for moving the needle/trocar 174 in the retraction direction. In a single, uninterrupted motion, the spring-biased linkage mechanism 182 moves from a pre-deployment position (FIG. 1) with both needle/trocar 174 and cannula 176 retracted (FIG. 2) to an intermediate position (FIG. 3) with both needle/trocar 174 and cannula 176 inserted (FIG. 4) to a post-deployment position (FIG. 5) with the needle/trocar 174 retracted and the cannula 176 inserted (FIG. 6).

Referring to FIGS. 7-12, one embodiment of the fluid drive mechanism 150 uses a clutch mechanism 160 to facilitate filling of the reservoir 130 and engagement of the fluid drive mechanism 150 for driving fluid out of the reservoir 130. The fluid drive mechanism 150 includes a first threaded member in the form of an elongated shaft such as a threaded drive rod or leadscrew 152, with external threads extending from a plunger 136 received in the reservoir 130 and sealed with an O-ring 137 against the inside surface of the reservoir 130. The leadscrew 152 and plunger 136 may be an inseparable, insert-molded assembly. A second threaded member in the form of an elongated shaft such as a tube nut 154 with internal threads threadably engages the leadscrew 152 and may be driven by a drive wheel 156 via a clutch mechanism 160.

When the reservoir 130 is empty (FIGS. 7 and 8), the plunger 136 is positioned at one end of the reservoir 130 such that the plunger 136 is extended and the clutch mechanism 160 is disengaged. In certain embodiments, the reservoir 130 may be filled with fluid, particularly insulin, by opening an inlet port to the reservoir 130 and pumping in the insulin under sufficient hydraulic pressure to retract the plunger 136 within the reservoir 130. Thereafter, the inlet port may be closed. When the reservoir 130 is filled and the plunger 136 moves to the opposite (retracted) end of the reservoir 130 (FIG. 9), the clutch mechanism 160 remains disengaged to allow the tube nut 154 to pass into an elongated cylindrical bore (along the drive axis) of a hub of the drive wheel 156. The clutch mechanism 160 may then be engaged (FIGS. 10-12) such that rotation of the drive wheel 156 causes the clutch mechanism 160 to rotate the tube nut 154, which causes the leadscrew 152 to advance the plunger into the reservoir 130 to deliver the fluid from the reservoir 130. In alternative embodiments, the reservoir 130 may be filled when the plunger 136 is already retracted.

Figure 7:
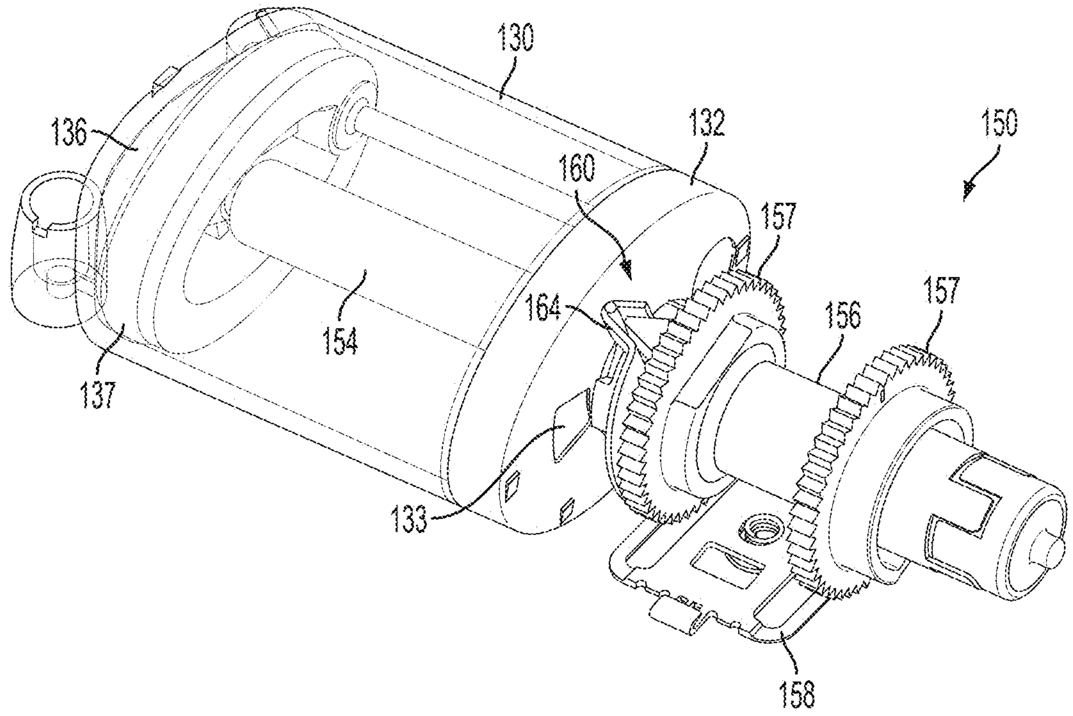
FIG. 7 is a top perspective view of a fluid driving mechanism of the fluid delivery device shown in FIG. 1 with a clutch mechanism in a disengaged position prior to filling.
Figure 8:
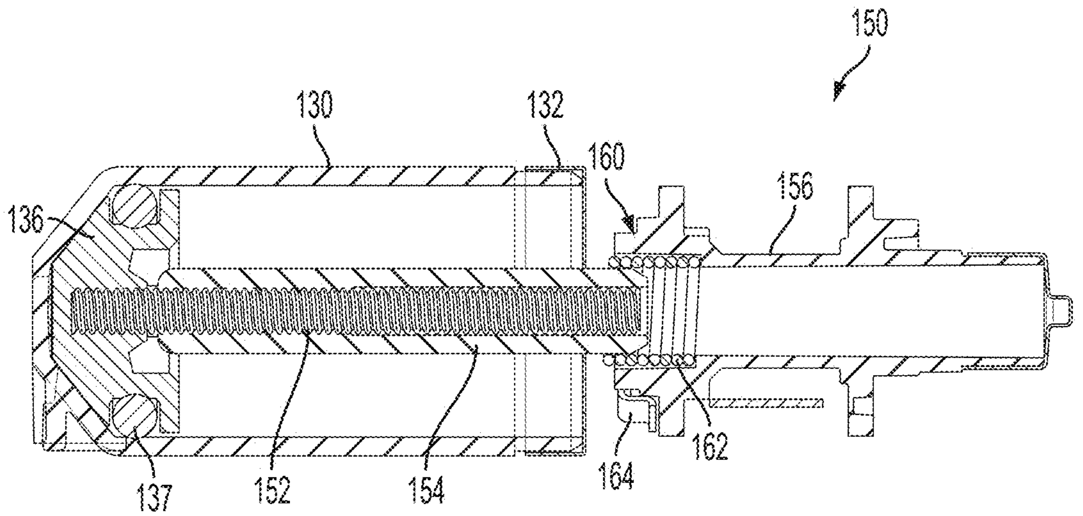
FIG. 8 is a side cross-sectional view of the fluid driving mechanism shown in FIG. 7.
Figure 9:
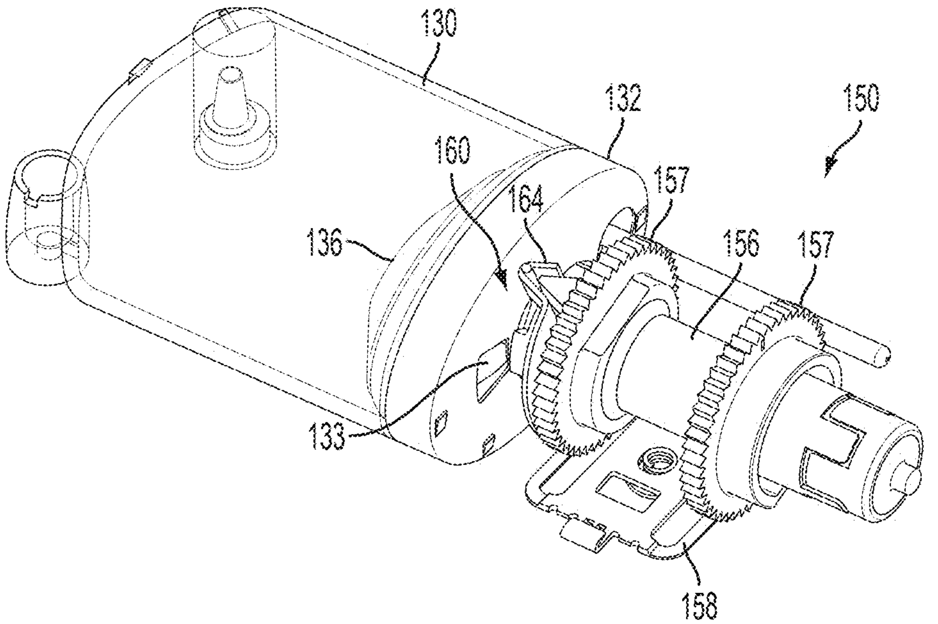
FIG. 9 is a top perspective view of the fluid driving mechanism shown in FIG. 7 with the clutch mechanism in a disengaged position after filling.
Figure 10:
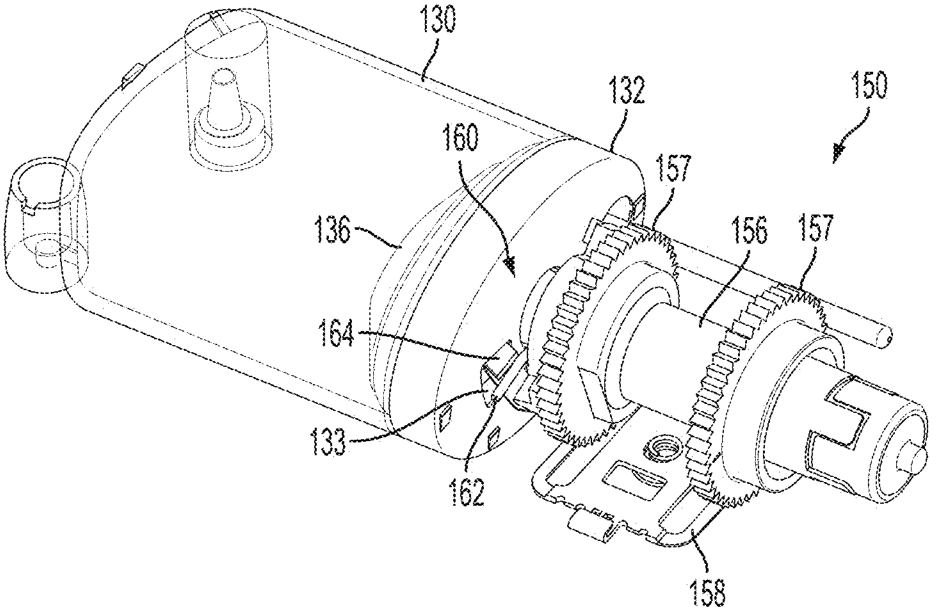
FIG. 10 is a top perspective view of the fluid driving mechanism shown in FIG. 7 with the clutch mechanism being released to the engaged position.
Figure 11:
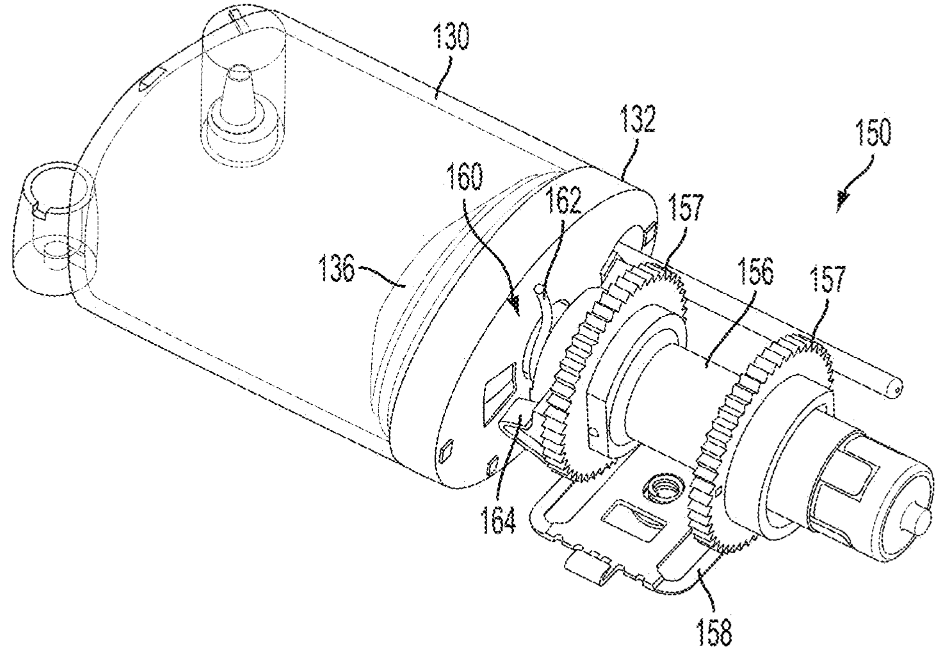
FIGS. 11 and 12 are top perspective views of the fluid driving mechanism shown in FIG. 7 with the clutch mechanism in the engaged position.
Figure 12:
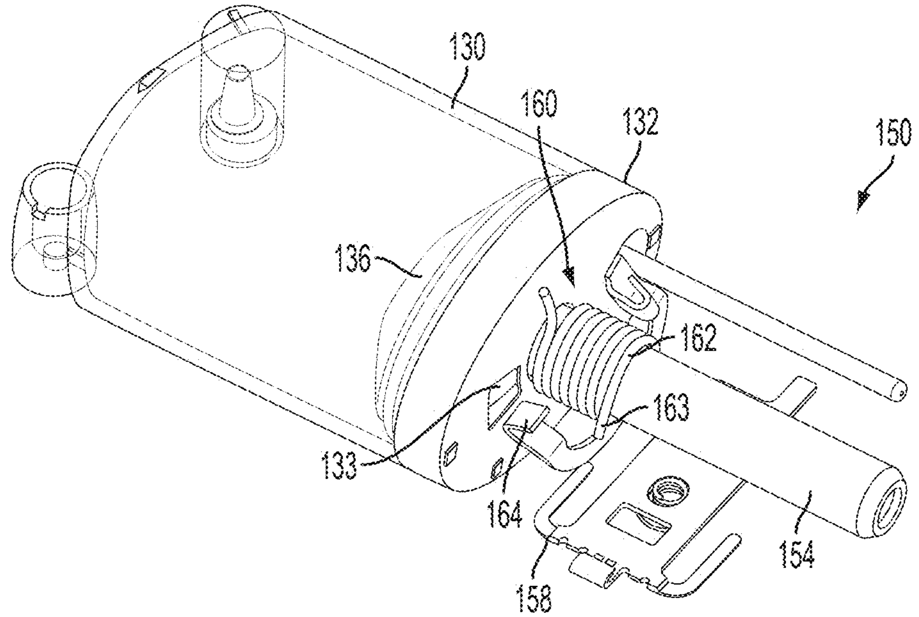

In the illustrated embodiment, the clutch mechanism 160 includes a clutch spring 162 (e.g., a helical torsion spring) located in a counterbore at one end of the drive wheel 156, adjacent the reservoir 130. The inside diameter of the clutch spring 162 is larger than the outside diameter of the tube nut 154 when the clutch spring 162 is loaded, thereby disengaging the clutch spring 162 from the tube nut 154 and allowing the tube nut 154 to pass through the center aperture of the clutch spring 162 and into the elongated bore of the drive wheel 156. Alternatively, the inside diameter of the clutch spring 162 is smaller than the outside diameter of the tube nut 154 when the clutch spring 162 is unloaded, thereby engaging or gripping the tube nut 154 and allowing the drive wheel 156 to rotate the tube nut 154. In the illustrated embodiment, prior to filing the reservoir 130, the clutch spring 162 is held in the loaded, disengaged position by a spring latch 164 engaged with the drive wheel 156 (FIGS. 7-9). After the reservoir 130 has been filled, the clutch spring 162 may thus be engaged by rotating the drive wheel 156 until the spring latch 164 releases the clutch spring 162 (FIG. 10) allowing the clutch spring 162 to unload and grip the tube nut 154 (FIGS. 11 and 12), at which time fluid may be dispensed from the reservoir 130 with continued rotation of the drive wheel 156.

As shown, the spring latch 164 may be biased by the clutch spring 162 such that as the drive wheel 156 rotates the spring latch 164 moves rotationally against a surface of a reservoir cap 132 until clutch spring 162 deflects the spring latch 164 into a window 133 in the reservoir cap 132. When the spring latch 164 moves into the window 133, the end of the clutch spring 162 held by the spring latch 164 is released, thus engaging the clutch mechanism 160. When the clutch spring 162 is engaged, the drive wheel 156 contacts an end 163 of the clutch spring 162 to create a thrust on the clutch spring 162 that causes the clutch spring 162 to rotate the tube nut 154. The fluid drive mechanism 150 may also use other clutch mechanisms capable of allowing the tube nut 154 or other type of nut or threaded member to pass through the clutch mechanism and then being activated to engage the nut or threaded member.

In the illustrated embodiment, the drive wheel 156 includes ratchets 157 that are engaged by an actuator 158 to incrementally drive the wheel 156 and advance the plunger 136 into the reservoir 130. Examples of this actuation mechanism are described in greater detail in U.S. Patent Application Publication No. 2005/0238507, which is fully incorporated herein by reference.

By using a clutch mechanism, the engagement between the leadscrew and the nut occurs at assembly, and thus no rotation is needed for the nut to engage the leadscrew by operation of the device. This reduces the number of fluid path prime pulses to prime the pump and assures a full and proper priming of the fluid path before placement on the body. The clutch mechanism also enables the changing of thread pitch for other drug applications without a need to redesign the tilt nut used in fluid driving mechanisms in other existing pumps. The components of the clutch mechanism are also more easily inspected than the tilt nut assembly.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A drive mechanism for a fluid delivery device, comprising:
- a plunger disposed within a reservoir;
- a leadscrew extending from the plunger;
- a nut threadably engaged with the leadscrew;
- a drive wheel; and
- a clutch mechanism coupled to the drive wheel, the clutch mechanism configured to allow the nut to pass through the clutch mechanism when disengaged and to couple the nut to the drive wheel when engaged, the drive wheel configured to rotate the nut to advance the leadscrew and the plunger into the reservoir while the clutch mechanism is engaged.

2. The drive mechanism of claim 1, wherein the nut comprises a tube nut.

3. The drive mechanism of claim 1, wherein the clutch mechanism includes a clutch spring configured to grip the nut when released to an engaged position.

4. The drive mechanism of claim 3, wherein the clutch mechanism includes a spring latch configured to hold the clutch spring in a disengaged position and to release the clutch spring to move to the engaged position.

5. The drive mechanism of claim 4, wherein the spring latch is
- configured to release the clutch spring in response to movement of the drive wheel.

6. The drive mechanism of claim 3, wherein the clutch spring comprises a helical torsion spring, the drive wheel includes a counterbore formed therein at an end of the drive wheel adjacent to the reservoir, and the helical torsion spring is located within the counterbore.

7. The drive mechanism of claim 6, wherein the drive wheel includes a bore formed therein, the bore axially aligned with the counterbore and configured to receive a portion of each of the leadscrew and the nut.

8. A fluid delivery device comprising:
- a fluid reservoir;
- a transcutaneous access tool fluidly coupled to the fluid reservoir; and
- a drive mechanism comprising:
  - a drive wheel;
  - a plunger received in the reservoir;
  - a leadscrew extending from the plunger;
  - a nut threadably engaged with the leadscrew; and
  - a clutch mechanism coupled to the drive wheel, the clutch mechanism configured to allow the nut to pass through the clutch mechanism when disengaged and to couple the nut to the drive wheel when engaged, the drive wheel configured to rotate the nut to advance the leadscrew and the plunger into the reservoir while the clutch mechanism is engaged.

9. The fluid delivery device of claim 8, wherein the nut comprises a tube nut.

10. The fluid delivery device of claim 8, wherein the clutch mechanism includes a clutch spring configured to grip the nut when released to an engaged position.

11. The fluid delivery device of claim 10, wherein the clutch mechanism includes a spring latch configured to hold the clutch spring in a disengaged position and to release the clutch spring to move to the engaged position.

12. The fluid delivery device of claim 11, wherein the spring latch is configured to release the clutch spring in response to movement of the drive wheel.

13. The fluid delivery device of claim 10, wherein the clutch spring comprises a helical torsion spring, the drive wheel includes a counterbore formed therein at an end of the drive wheel adjacent to the reservoir, and the helical torsion spring is located within the counterbore.

14. The fluid delivery device of claim 13, wherein the drive wheel includes a bore formed therein, the bore axially aligned with the counterbore and configured to receive a portion of each of the leadscrew and the nut.

15. The fluid delivery device of claim 8, wherein:
- when the reservoir is empty, the plunger is positioned at one end of the reservoir in an extended orientation and the clutch mechanism is disengaged; and
- when the reservoir is filled and the plunger is positioned at an opposite end of the reservoir in a retracted orientation, the clutch mechanism remains disengaged to allow the nut to pass into an elongated cylindrical bore along a drive axis of a hub of the drive wheel.

16. A drive mechanism for a fluid delivery device, comprising:
- an elongated assembly including a first elongated member and a second elongated member, wherein the first elongated member is configured to extend from a plunger within a reservoir and the second elongated member is coupled to the first elongated member;
- a drive wheel; and
- a clutch mechanism coupled to the drive wheel, wherein the clutch mechanism is configured to allow the second elongated member to pass through the clutch mechanism when disengaged and is configured to couple the second elongated member to the drive wheel when engaged, the drive wheel configured to rotate the second elongated member to advance the first elongated member and the plunger into the reservoir while the clutch mechanism is engaged.

17. The drive mechanism of claim 16, wherein the clutch mechanism includes a clutch spring configured to grip the second elongated member when released to an engaged position.

18. The drive mechanism of claim 17, wherein the clutch mechanism includes a spring latch configured to hold the clutch spring in a disengaged position and to release the clutch spring to move to the engaged position.

19. The drive mechanism of claim 17, wherein the clutch spring comprises a helical torsion spring, the drive wheel includes a counterbore formed therein at an end of the drive wheel adjacent to the reservoir, and the helical torsion spring is located within the counterbore.

20. The drive mechanism of claim 19, wherein the drive wheel includes a bore formed therein, the bore axially aligned with the counterbore and configured to receive a portion of each of the first elongated member and the second elongated member.

21. A drive mechanism for a fluid delivery device, comprising:
- a drive wheel including a recess comprising a pocket and an axially aligned through-hole;
- a resiliently biased gripping member seated within the pocket of the recess;
- a transmission element configured to convert rotational motion into axial motion of a plunger; and
- a clutch mechanism operable between:
  - a disengaged state, in which the transmission element is permitted to translate axially through the axially aligned through-hole of the recess without contacting the resiliently biased gripping member, and
  - an engaged state, in which rotational motion of the drive wheel is transmitted to the transmission element via the resiliently biased gripping member engaging the transmission element.

* * * * *